(12) United States Patent
Yasunaga et al.

(10) Patent No.: US 11,723,541 B2
(45) Date of Patent: Aug. 15, 2023

(54) DIAGNOSTIC METHOD, METHOD FOR VALIDATION OF DIAGNOSTIC METHOD, AND TREATMENT METHOD

(71) Applicant: TERUMO KABUSHIKI KAISHA, Tokyo (JP)

(72) Inventors: Mitsuteru Yasunaga, Fujinomiya (JP); Atsushi Nomura, Tokyo (JP); Kohtaroh Kusu, Fujinomiya (JP); Yusuke Sekine, Chigasaki (JP); Haruhiko Kamijo, Hando (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 464 days.

(21) Appl. No.: 16/170,508

(22) Filed: Oct. 25, 2018

(65) Prior Publication Data

US 2019/0117087 A1    Apr. 25, 2019

(30) Foreign Application Priority Data

Oct. 25, 2017    (JP) ................................. 2017-206694

(51) Int. Cl.
*A61B 5/02* (2006.01)
*A61B 5/00* (2006.01)
(Continued)

(52) U.S. Cl.
CPC ........ *A61B 5/02007* (2013.01); *A61B 5/0082* (2013.01); *A61B 5/05* (2013.01); *A61B 5/4836* (2013.01); *A61B 5/7221* (2013.01); *A61B 5/7267* (2013.01); *A61B 6/504* (2013.01); *A61B 6/5217* (2013.01); *A61B 6/5247* (2013.01); *A61B 8/085* (2013.01); *A61B 8/0891* (2013.01); *A61B 8/5261* (2013.01); (Continued)

(58) Field of Classification Search
None
See application file for complete search history.

(56) References Cited

U.S. PATENT DOCUMENTS 7,901,348 B2 * 3/2011 Soper ................. A61B 1/00009
600/117
9,642,586 B2    5/2017 Kelm et al.
(Continued)

FOREIGN PATENT DOCUMENTS

JP    2009-273640 A    11/2009
JP    2017079914 A    5/2017

OTHER PUBLICATIONS

Guidotti et al., "A Survey of Methods for Explaining Black Box Models", ACM Computing Surveys, Aug. 2018, pp. 93:1-93:42, vol. 51, No. 5, article 93.
(Continued)

*Primary Examiner* — Katherine L Fernandez
(74) *Attorney, Agent, or Firm* — Buchanan Ingersoll & Rooney PC

(57) ABSTRACT

A method is disclosed for diagnosing and treating a patient having lesions in both arteries of left and right lower limbs. By determining that a lesion distal to an aortailiac bifurcation is to be treated first, catheters and an operation time can be reduced is to be treated first on a priority basis based on diagnostic data, deciding that a lesion proximal to the bifurcation is to be treated next, then treating the lesions substantially continuously.

18 Claims, 24 Drawing Sheets

(51) Int. Cl.
    *A61B 6/00*     (2006.01)
    *A61B 8/08*     (2006.01)
    *G16H 50/20*     (2018.01)
    *A61B 5/05*     (2021.01)
    *G16H 20/40*     (2018.01)
    *G06V 10/44*     (2022.01)
    *G06F 18/21*     (2023.01)
    *G06F 18/2413*     (2023.01)
    *G06V 10/764*     (2022.01)
    *G06V 10/82*     (2022.01)
    *A61M 25/06*     (2006.01)
    *G06V 40/14*     (2022.01)

(52) U.S. Cl.
    CPC ...... *G06F 18/217* (2023.01); *G06F 18/24133* (2023.01); *G06V 10/454* (2022.01); *G06V 10/764* (2022.01); *G06V 10/82* (2022.01); *G16H 20/40* (2018.01); *G16H 50/20* (2018.01); *A61B 8/5223* (2013.01); *A61B 2576/02* (2013.01); *A61M 2025/0681* (2013.01); *G06V 40/14* (2022.01); *G06V 2201/03* (2022.01)

(56) References Cited

U.S. PATENT DOCUMENTS

| | | | |
|---|---|---|---|
| 10,133,846 | B2 | 11/2018 | Takata et al. |
| 2007/0092864 | A1* | 4/2007 | Reinhardt ............... A61B 90/36 435/4 |
| 2009/0156895 | A1* | 6/2009 | Higgins ................. G06T 19/003 600/104 |
| 2011/0118595 | A1 | 5/2011 | Aulbech et al. |
| 2012/0220840 | A1 | 8/2012 | Morita et al. |
| 2014/0358123 | A1* | 12/2014 | Ueda ................. A61M 25/0053 604/510 |
| 2015/0051480 | A1 | 2/2015 | Hwang et al. |
| 2015/0087957 | A1 | 3/2015 | Liu et al. |
| 2015/0117730 | A1 | 4/2015 | Takayama |
| 2015/0157802 | A1 | 6/2015 | Yoon |
| 2015/0265162 | A1 | 9/2015 | Lavi et al. |
| 2015/0379708 | A1 | 12/2015 | Abramoff et al. |
| 2016/0045180 | A1 | 2/2016 | Kelm et al. |
| 2016/0148371 | A1 | 5/2016 | Itu et al. |
| 2016/0157802 | A1 | 6/2016 | Anderson |
| 2016/0157807 | A1 | 6/2016 | Anderson et al. |
| 2017/0076014 | A1 | 3/2017 | Bressloff |
| 2017/0281131 | A1 | 10/2017 | Sendai |
| 2017/0311917 | A1 | 11/2017 | Allmendinger et al. |
| 2018/0078313 | A1 | 3/2018 | Comaniciu et al. |
| 2018/0243033 | A1 | 8/2018 | Tran et al. |
| 2019/0117088 | A1 | 4/2019 | Nomura et al. |
| 2019/0117089 | A1 | 4/2019 | Nomura et al. |
| 2019/0117090 | A1 | 4/2019 | Ishii et al. |
| 2019/0117181 | A1 | 4/2019 | Ishii et al. |
| 2019/0125192 | A1 | 5/2019 | Kusu et al. |
| 2019/0125193 | A1 | 5/2019 | Saito et al. |
| 2019/0125194 | A1 | 5/2019 | Sekine et al. |
| 2019/0125287 | A1 | 5/2019 | Itou et al. |
| 2019/0150867 | A1 | 5/2019 | Itou et al. |
| 2019/0121291 | A1 | 8/2019 | Otake et al. |
| 2019/0231291 | A1 | 8/2019 | Otake et al. |
| 2020/0093543 | A1 | 3/2020 | Takahashi et al. |
| 2020/0126229 | A1 | 4/2020 | Lavi et al. |
| 2020/0155079 | A1 | 5/2020 | Kusu et al. |
| 2020/0155101 | A1 | 5/2020 | Yasunaga et al. |
| 2021/0085397 | A1* | 3/2021 | Passerini ............. G06N 3/0454 |

OTHER PUBLICATIONS

Sanghvi et al., "Transradial Intervention of Iliac and Superficial Femoral Artery Disease is Feasible", Journal of Interventional Cardiology, 2008, pp. 385-387, vol. 21, No. 5.

Macedo et al.: "A bifurcation identifier for IV-OCT using orthogonal least squares and supervised machine learning," Computerized Medical Imaging and Graphics 46 (2015), pp. 237-248.

Alberti et al.: "Automatic Bifurcation Detection in Coronary IVUS Sequences," IEEE Transactions on Biomedical Engineering, vol. 59, No. 4, Apr. 2012, pp. 1022-1031.

\* cited by examiner

DIAGNOSTIC METHOD, METHOD FOR VALIDATION OF DIAGNOSTIC METHOD, AND TREATMENT METHOD

CROSS-REFERENCES TO RELATED APPLICATIONS

This application claims priority from Japanese Patent Application No. 2017-206694 filed on Oct. 25, 2017, the entire contents of which are incorporated herein by reference.

FIELD OF THE INVENTION

The present disclosure generally relates to a method of diagnosing which of one or more lesions in each of a plurality of blood vessels bifurcated from a blood vessel having bifurcations is to be treated first for treating the blood vessel by an intervention procedure.

BACKGROUND DISCUSSION

In the related art, ipsilateral puncture in which a catheter is introduced from an artery on the same leg as that having a lesion, or a contralateral puncture (cross-over method) in which the catheter is introduced from a leg opposite from the leg having the lesion have been employed in order to treat an arterial lesion of a lower limb of a biological lumen having a lesion and a bifurcation. However, in recent years, a method of treating by introducing a catheter from an artery of an arm, specifically, a radial artery (TRI: Trans Radial Intervention) may be performed with relatively less physical burden to patients and a relatively shorter stay in the hospital.

For example, Journal of Interventional Cardiology Volume 21, Issue 5 October 2008 Pages 385-387 Transradial Intervention of Iliac and Superficial Femoral Artery Disease is Feasible discloses that a catheter is introduced from an arm to treat percutaneously the iliac artery and a superficial femoral artery (SFA).

U.S. Patent Publication No. 2014/0358123 also discloses a dual catheter assembly configured to be inserted from an arm for treating a lesion of a lower limb artery and a method of continuously treating lesions of left and right lower limbs by optionally selecting the lesion to be treated first.

JP-A-2017-79914 discloses a method of diagnosing a treatment method by determining whether a guide wire can pass through a lesion with an index CT value indicating the calcification degree of an X-ray CT (computer tomography) image.

Furthermore, U.S. Pat. No. 9,642,586 discloses a method of reading medical diagnostic images by machine-learning, and ACM Computing Surveys, Vol. 51, No. 5, Article 93. Publication date: August 2018 discloses that interpretation is necessary in deep learning in which classification of images is concealed.

Although Journal of Interventional Cardiology Volume 21, Issue 5 October 2008 Pages 385-387 Transradial Intervention of Iliac and Superficial Femoral Artery Disease is Feasible discloses treatment of lower limb arteries with TRI, there is no description about placing a distal end of a guiding catheter beyond an aortailiac bifurcation and treatment to be performed when lesions are located in both bifurcations.

U.S. Patent Publication No. 2014/0358123 also describes a method of continuously treating lesions present respectively in blood vessels of bifurcated right and left lower limbs. However, the order of treatment is optional.

In addition, although JP-A-2017-79914 discloses software for determining whether the guide wire can pass depending on the degree of calcification, that is, hardness based on X-ray CT image diagnosis. JP-A-2017-79914 does not disclose temporal factors, that is, which lesion is to be treated first and which is more advantageous to the patient.

In contrast, ACM Computing Surveys, Vol. 51, No. 5, Article 93. Publication date: August 2018 discloses that machine-learning using deep learning is concealed, and interpretation is necessary. In contrast, U.S. Pat. No. 9,642,586 discloses an image diagnostic method based on machine-learning using deep learning. However, U.S. Pat. No. 9,642,586 is only for classification and the process of diagnosis is concealed and the reason is not clearly specified.

In Article 1-4 (2) of the Medical Care Law of Japan, there is a description "Physicians, dentists, pharmacists, nurses and other providers of medical care shall endeavor to provide appropriate explanations and obtain the understanding of those who receive medical care for providing healthcare". Therefore, the diagnosis and treatment cannot be carried out unless the explanation (informed consent) is made.

In contrast, there has been no diagnostic method which is established by performing treatment by physicians based on diagnoses, revalidating prognosis, and validating and correcting the method of diagnosis. Moreover, there has been no known diagnostic method that automatically corrects reasons for determination in diagnostic based on reinforcement-learning using the result of treatment as remuneration and improves diagnostic accuracy.

However, even in the same lower limb arteries, differences in distance from an aortailiac bifurcation may cause differences in effects of treatment and treatment difficulties.

Shortening an operation time depending on which lesion in the bifurcated blood vessels each having one or more lesions is to be treated first and efficiently using the guiding catheter or a therapeutic catheter is important for reducing the relative burden on patients, shortening or reducing time spent for the procedure, shortening time of using an operating room, and reducing the number of catheters to be use, that is, in terms of medical economics.

SUMMARY OF INVENTION

A method is disclosed for diagnosing lesions in a plurality of bifurcated lumens, the plurality of bifurcated lumens being connected to a biological lumen via a bifurcation from a main lumen, including: detecting electromagnetic waves obtained through a patient by irradiating the patient with electromagnetic waves, and obtaining electromagnetic wave information on the patient based on a changed electromagnetic wave; identifying one or more of the lesions from the electromagnetic wave information; determining to extract distance information from the bifurcation to the respective lesions from the electromagnetic wave information when there are a plurality of the lesions; acquiring the distance information; and determining that a lesion proximal to the lesion is to be treated first among the plurality of lesions based on the distance information.

In the diagnostic method according to the present disclosure, when there is one lesion present in each of the plurality of bifurcated lumens, the lesion that is to be treated first is determined to be the lesion proximal to the bifurcation based on the distance information.

In the diagnostic method according to the present disclosure, in a case where the main lumen is an aorta, the bifurcation is an aortailiac bifurcation, and the plurality of bifurcated lumens are left and right lower limb arteries, and the left and right lower limb arteries each have the lesion, it is determined from the bifurcation that the distance information is obtained, and the lesion proximal to the bifurcation of the lesion is to be treated first based on the distance information.

In the diagnostic method according to the present disclosure, the lesion proximal to the bifurcation is determined to be treated first, and then the lesion distal to the bifurcation is determined to be treated subsequently.

In the diagnostic method according to the present disclosure, the treatment is a treatment of the lesion by using a catheter inserted from a radial artery of an arm.

In the diagnostic method according to the present disclosure, the electromagnetic waves are selected from at least one of X-rays, magnetic field lines, ultrasound waves, infrared rays, and visible light.

In the diagnostic method according to the present disclosure, the diagnosis is performed by artificial intelligence.

In the diagnostic method according to the present disclosure, based on the distance information, the determining that the lesion proximal to the bifurcation is to be treated first among the plurality of lesions is performed by deep learning.

In the diagnostic method according to the present disclosure, the diagnosis is performed by reinforcement-learning using a result of treatment.

A validation method is disclosed for diagnosing lesions in a plurality of bifurcated lumens, the plurality of bifurcated lumens being connected to a biological lumen via a bifurcation from a main lumen, including: detecting electromagnetic waves obtained through a patient by irradiating the patient with electromagnetic waves, and obtaining electromagnetic wave information on the patient based on a changed electromagnetic wave; identifying one or more of the lesions from the electromagnetic wave information; determining to extract distance information from the bifurcation to the respective lesions from the electromagnetic wave information when there are a plurality of the lesions; acquiring the distance information; and determining that a lesion proximal to the bifurcation is to be treated first among the plurality of lesions based on the distance information, wherein the distance information is used.

In the validation method according to the present disclosure, the validation method uses information that the lesion to be treated first is the lesion proximal to the bifurcation.

In the validation method according to the present disclosure, the validation method uses other information on a patient after treatment.

In the validation method according to the present disclosure, the validation method is performed based on reinforcement-learning using other information on the patient after treatment as remuneration.

A treatment method according to the present disclosure is, a method of treating a patient having a lesion in each of the left and right lower limb arteries connected via an aortoiliac bifurcation to an aorta, including: verifying which of the respective lesions is more proximal to the aortailiac bifurcation based on diagnostic information on a patient, and determining that the lesion proximal to the bifurcation is to be treated first; introducing a catheter from an artery of an arm of the patient, advancing and placing a catheter tip of the catheter to at least the aortailiac bifurcation of the patient; and inserting a therapeutic catheter into a lumen of the catheter in position, projecting the therapeutic catheter tip of the therapeutic catheter from the catheter tip, and treating the lesion proximal to the bifurcation first, and then projecting the therapeutic catheter tip from the catheter tip to treat the lesion distal to the bifurcation.

In the treatment method according to the present disclosure, the catheter is also used in the treating the lesion distal to the bifurcation.

In the treatment method according to the present disclosure for achieving the above-described object, the therapeutic catheter is also used in the treating the lesion distal to the bifurcation.

In the treatment method according to the present disclosure, the therapeutic catheter is removed from the catheter after treating the lesion proximal to the bifurcation, and a second therapeutic catheter is used in the treating the lesion distal to the bifurcation.

In the treatment method according to the present disclosure, the catheter is a guiding catheter, and a catheter assembly including an inner catheter inserted in a lumen of the guiding catheter is used in the placing.

In the treatment method according to the present disclosure, the diagnostic information is image information on the patient.

In the treatment method according to the present disclosure, the treatment method includes measuring a distance from the bifurcation to the lesion first from the image information.

According to the present disclosure, to select that a lesion proximal to a bifurcation is to be treated first may be diagnosed by a person, or artificial intelligence, for example, preferably by machine-learning by using electromagnetic wave information obtained from electromagnetic waves irradiated to a patient, for example, by using X-ray angiographic image information.

Furthermore, the machine-learning can diagnose only from the information on the distance from the bifurcation before being converted into an image recognizable by a person. Alternatively, which lesion is to be treated first may be determined through diagnosis based on the information on the distance from the bifurcation, for example, preferably, information on the lesion proximal to the bifurcation obtained from an image of high resolution exceeding a resolution of human eyes or electromagnetic wave information before image processing.

Furthermore, by validating the diagnostic method, the reason for the diagnostic method can be clarified, and for example, image information data in the past in the hospital, a clinical case on big data, images generated by simulation, and the like may be used for similar clinical conditions. Accordingly, since time required for diagnosis may be shortened without trial and error, they may be used as a criterion for assistance of diagnosis by a physician or diagnosis and treatment by artificial intelligence.

In order to treat a patient with lesions in arteries of both left and right legs connected to an aortailiac bifurcation by a diagnosis by human or machine-learning, according to the present disclosure, deformation in shape or deterioration of the catheter due to the treatment being passed through the significantly bent blood vessels is eliminated by treating the lesion proximal to the aortailiac bifurcation first to treat a patient with lesions in both of the left and right lower limb arteries, and efficient treatment of the left and right blood vessels is achieved by maintaining the blood vessel selectivity for the catheter for the subsequent treatment.

In addition, treatment with certainty can be achieved by efficiently using the catheter while maintaining blood vessel selectivity and capability of passing the blocked portion of a guide wire and the catheter to be used for treatment.

Furthermore, when a catheter assembly using the catheter as a guiding catheter and having an inner catheter placed in the lumen is used, the guiding catheter may be relatively easily placed near the lesion distal to the bifurcation where the placement can be difficult.

In addition, by validating the result of treatment by machine-learning, the effects of treatment may be validated, accuracy of treatment can be improved, and at the same time, future predictions such as standardization of treatment by utilizing big data can be achieved.

Accordingly, speed can be improved, costs can be reduced, working hours can be shortened, and labor costs can be reduced, thereby contributing to medical economics.

DETAILED DESCRIPTION

Figure 1:
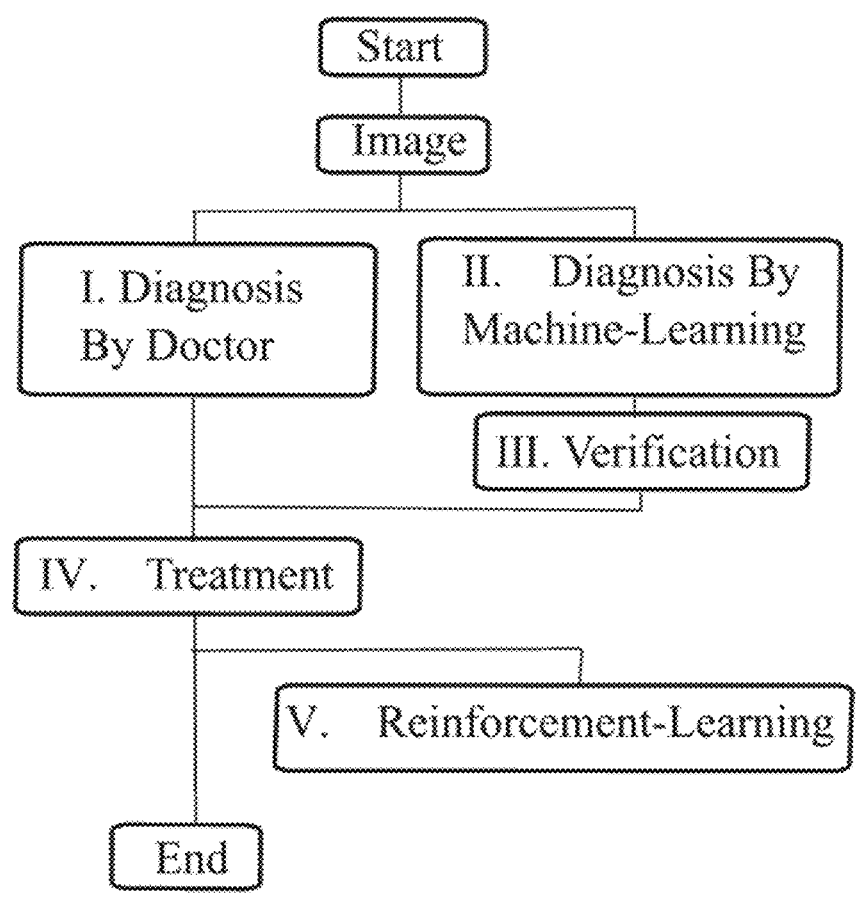
FIG. 1 is a general explanatory drawing illustrating a flow of a diagnostic method according to an embodiment.

First, a diagnostic method will be described. Diagnosis refers to examining patients by physicians to determine their disease condition, and the diagnostic method can be performed not only by a person, but also by artificial intelligence (hereinafter, referred to as AI), specifically, by machine-learning. As illustrated in FIG. 1, the diagnostic method first acquires patient information from a patient. The physician, who is a person, diagnoses the patient's condition from the patient information such as X-ray angiographic images (I), and performs treatment as needed (IV).

Alternatively, when artificial intelligence, which is machine-learning, supports or performs the diagnosis based on the patient information, the diagnosis is performed by using, for example, the image information based on the machine-learning (II), and after verification (III), information is provided to a physician to support diagnosis or treatment by the physician.

If possible, the artificial intelligence itself with machine-learning performs diagnosis or treatment.

Support, diagnosis or treatment of a diagnosis based on reinforcement-learning with a result of treatment as remuneration (V) may also be performed.

I. Diagnostic Method

The present diagnostic method is a diagnostic method for determining a lesion to be treated first from lesions located in the bifurcated lumen in a biological lumen in which a plurality of bifurcated lumens are connected via a bifurcation from a main lumen.

Biological lumens to be treated include gastrointestinal tract, lymphatic vessels, blood vessels, and preferably, blood vessels and more preferably, arteries. Arteries include blood vessels of the head, arms, heart, aorta, various organs, and lower limbs. When the main lumen is an aorta, the bifurcations include an aortailiac bifurcation, an aortic root of subclavian artery, an aortic root of brachiocephalic artery, and an aortic root of aortic common carotid artery, and preferably, an aorta iliac artery, while the plurality of bifurcated lumens connected via the bifurcation include left and right lower limb arteries, specifically, the left common iliac artery and the right common iliac artery, and more peripheral arteries of the lower limbs connected to left common iliac artery and the right common iliac artery.

When the blood vessel bifurcated from the aorta is considered to be the main lumen, the bifurcations may include a subclavian artery-left tibial artery bifurcation, a brachiocephalic artery-right common carotid artery root, and an external carotid artery-internal carotid artery bifurcation.

In the heart, in a case of the left coronary artery, the main trunk of the left coronary artery may be considered to be a main lumen, and the connected bifurcated lumens may include the left circumflex artery, the left anterior descending artery and more peripheral arteries connected to the left coronary artery, or bifurcated arteries connected to more peripheral bifurcations. In the case of the right coronary artery, when the right coronary artery is considered to be a main lumen, connected branch arteries are also applicable. Alternatively, when an ascending aorta is assumed to be the main lumen, the bifurcated lumen connected to the ascending aorta may be the left coronary artery and the right coronary artery. Blood vessels bifurcated from the aorta may be an inferior mesenteric artery (IMA), a superior mesenteric artery (SMA), a celiac artery, a renal artery, or even a collateral circulation.

Diagnosis of one or more lesions at the bifurcation of the lower limb arteries by TRI has been described.

Blood vessels bifurcated from blood vessels bifurcated from the aorta may include an inferior mesenteric artery (IMA), a superior mesenteric artery (SMA), the celiac artery, the renal artery, or blood vessels bifurcated from the collateral circulation such as a bifurcated blood vessel from a hepatic artery.

For example, Transcatheter Arterial Embolization (TAE) transcatheter arterial embolization therapy and Transcatheter Arterial Chemical Embolization (TACE) Hepatic Artery Chemoembolization are targeted to lesions of the tumor, which may have multiple vasa vasorum. For example, to help make sure that cancer cells are killed, blocking the lesion proximal to the bifurcation is determined by diagnosis. When viewed from the upstream side (heart side), treatment of the lesion proximal to (heart side) the bifurcation is more effective because the blood vessel is thicker. After determining the therapeutic effect, if it is insufficient, whether the lesion distal to the bifurcation is to be blocked may be determined.

Particularly preferred is the artery of the lower limb, but may also be the right common iliac artery and the left common iliac artery at the aortailiac bifurcation, and also an external iliac artery and an internal iliac artery bifurcated respectively from the left and right common iliac artery, the common femoral artery extending from the external iliac artery, a superficial femoral artery and a deep femoral artery bifurcated from the femoral artery, or more peripheral popliteal arteries (BTK: below the knee) or an anterior tibial artery, a peroneal artery, a posterior tibial artery, a dorsalis pedis artery, a plantar artery, and other peripheral arteries or even the collateral circulation.

More favorable parts to be treated because of the high expected effects of treatment include the aortailiac bifurcation, the left and right common iliac artery, the external iliac artery and the internal iliac artery, the common femoral artery, the superficial femoral artery and the deep femoral artery, and the popliteal artery (BTK).

The catheter is introduced into an ulnar artery or a radial artery out of the arteries of the arm, but more preferably, into the radial artery (RADIAL). The radial artery may be of either left or right, but if the distance from the bifurcation to the lesion is relatively large, left TRI, which is an anatomically shorter distance from a puncture site to the lesion, is preferred. If the patient's blood vessel is narrow, puncturing from right TRI may be selected through diagnosis for treatment from the reasons such that the blood vessel of the dominant arm is relatively thicker or easier to puncture, or free from spasm, or relatively easier for the surgeon to perform the procedure from the puncture site.

Alternatively, the radial artery (Radial) near the wrist, the distal radial artery, or the radial artery in Snuff box (i.e., anatomical snuff box) can be used. Here, the radial artery in the Snuff box is a radial artery located on the peripheral side of the radial artery between the short maternal extensor tendon and the long maternal extensor tendon, and is referred to as s-RA. The distal radial artery is the dorsal carpal bifurcation of the radial artery, is the radial artery located between the long maternal extensor tendon and the tendon of an extensor carpi radialis longus muscle, which are referred to as d-RA hereinafter.

For example, access from Radial or s-RA or d-RA can be relatively less invasive, and can be preferable because of the shorter hospitalization period. In particular, for example, if s-RA or d-RA is the left TRI, placing a patient's left wrist on a patient's abdomen can be more preferable because the surgeon is allowed to stand on a right side of the patient, which can be relatively easier in terms of posture and less exposed.

In contrast, if the radial access is determined to be difficult, or when it is determined that the distance from Radial to the bifurcation and lesion is relatively far, that it takes time, or that there is no device to reach, the access may be selected from a transbrachial artery intervention (TBI), a transfemoral artery intervention (TFI), or more peripheral popliteal artery (BTK), the anterior tibial artery, the peroneal artery, the dorsalis pedis artery, the plantar artery, the posterior tibial artery and other peripheral arteries, or even by retroactive puncture from the collateral circulation through diagnosis.

To identify the lesions of these biological lumens, in accordance with an exemplary embodiment, patient information is acquired. The patient information can include electromagnetic wave information, medical record information, other nonclinical periodical information, big data, etc., of patients' lesions.

As used herein the term "electromagnetic wave information" is intended to mean, among patient information, electromagnetic waves detected by irradiating a human body with electromagnetic waves which have been changed due to transmission, absorption, reflection or the like of a medical device or a medicine or the like that has been implanted or inserted into the human body.

In accordance with an exemplary embodiment, for example, the patient is irradiated with electromagnetic waves, and electromagnetic waves obtained through the patient are detected, and then the electromagnetic wave information on the patient is obtained based on the changed electromagnetic wave. At least one or more lesions are identified from the electromagnetic wave information, and extraction of the distance information from the bifurcation to the lesion from the electromagnetic wave information is determined, and the distance information is obtained, and then the lesion to be treated first is determined based on the distance information. Preferably, when there is one lesion present in each of the plurality of bifurcated lumens, it is determined, based on the distance information, that the lesion proximal to the bifurcated lumens is to be treated first.

For example, the irradiation energy can include X-rays, ultrasonic waves, infrared rays, visible light, magnetic field lines, and the like, and if the irradiation energy is distant from the human body, an X-ray is more preferable, and if the irradiation energy is in contact with or within a human body, ultrasound waves and visible light are more preferable. When one or more energies are used, a combination of ultrasonic waves and near-infrared rays is also applicable. In a case where X-rays are used as electromagnetic waves, when contrast agent is injected into the blood vessel and the X-ray is irradiated, the portion of the body containing a large amount of the contrast agent transmits a relatively lesser amount of X-rays, and therefore the amount of the electromagnetic wave information is decreased.

The electromagnetic wave information may be detected by a method of detecting on a plane opposite from an irradiation source with a human body interposed in between such as an FPD (flat panel detector), or may be detected over a whole circumference, such as a CT scan. The incident X-rays are converted to light by a CsI (thallium active cesium iodide) scintillator, and light signals are then converted into electrical signals by a photodiode of each pixel. The electrical signal of each pixel is read through a thin film transistor (TFT) switch connected to the photodiode, and X-ray image information is formed by the operation of an analog/digital (ND) conversion element, a low noise amplifier circuit, and the like.

When a scintillator, for example, having a width of 0.1 mm is arranged on the largest 17 inch FPD currently on the market, it corresponds to approximately 4300×4300 elements, and each element detects analog electromagnetic wave information, and then outputs the detected analogue electromagnetic wave information as a digital signal having at least 16 gradations, more preferably, 256 gradations.

Usually, formed X-ray image information is used for image classification by diagnosis or machine-learning.

Next, from the image information, a determination can be made if a lesion is present or not. In determination, conventional techniques such as Trans-Atlantic Inter-Society Consensus (TASC) II and ABI may be used or, as risk factors for ankle-bronchial pressure index (ABI) and peripheral arterial disease (PAD), information such as (1) aged persons of 70 years old or older, (2) persons of 50 to 70 years old but have a history of smoking or diabetes, (3) persons having any symptom, that is, a symptom in lower limbs or physical depression due to an exercise load, (4) when abnormality is found in lower limb blood vessel inspection, (5) when an evaluation of cardiovascular risk, which is an index for arteriosclerotic disease, is undesirable may also be used.

Alternatively, a method in conformity with a new guideline described in a newly provided PAD treatment guideline, 2017 ESC Guidelines on the Diagnosis and Treatment of Peripheral Arterial Diseases, in collaboration with the European Society for Vascular Surgery (ESVS): Document covering atherosclerotic disease of extracranial carotid and vertebral, mesenteric, renal, upper and lower limb arteries (The Task Force for the Diagnosis and Treatment of Peripheral Arterial Diseases of the European Society of Cardiology (ESC) and of the European Society for Vascular Surgery (ESVS) (European Heart Journal, Volume 39, Issue 9, 1 Mar. 2018, Pages 763-816) may also be employed.

Figure 2:
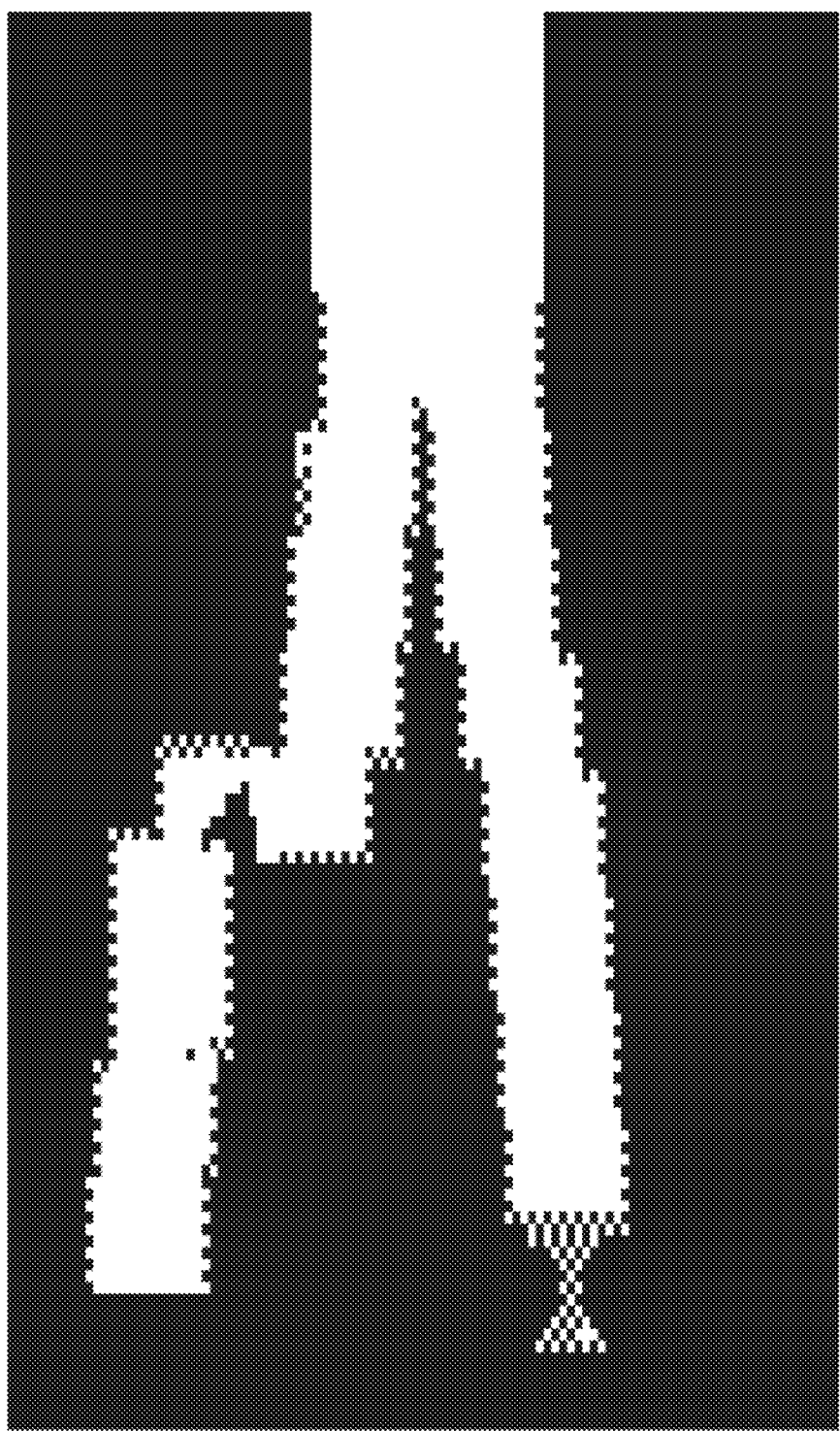
FIG. 2 is a schematic diagram of X-ray imaging information on a lesion in each of left and right lower limb arteries of lower limbs in artery to which a left lower limb artery and a right lower limb artery are connected from an aorta through an aortailiac bifurcation of the diagnostic method according to the embodiment.

In accordance with an embodiment, for example, a pulsatile flow pump is attached to a silicon blood vessel model, a tip of an imaging catheter introduced from the radial artery is advanced to the aorta, iopamiron, which is an iodinated contrast agent, can be injected into the radial artery and the aorta, for example, by using a commercially available X-ray imaging apparatus (a tube voltage of 120 KV, a tube current of 400 mA), and the left and right common iliac arteries connected to the aorta and the aortailiac bifurcation and the more peripheral lower limb arteries are imaged. FIG. 2 shows a virtual X-ray angiographic image taken in this manner.

In the virtual X-ray angiographic image, when the iopamiron is injected, portions corresponding to blood vessels with a high flow rate of contrast agent, for example, with a large blood flow, have a large X-ray contrast, for example, electromagnetic waves are absorbed and thus a small amount of electromagnetic wave information can be detected. In contrast, portions corresponding to blood vessels with a small blood flow, such as a stenosed site, have a small X-ray contrast and thus a large number of electromagnetic wave information can be detected. When binarizing portions detected a small amount of electromagnetic wave information and portions detected a large amount of electromagnetic wave information and expressing in white and black respectively, an obtained image includes portions having a large amount of blood flow in which the contrast agent flows in while and stenosed sites where blood does not flow in black.

Figure 3:
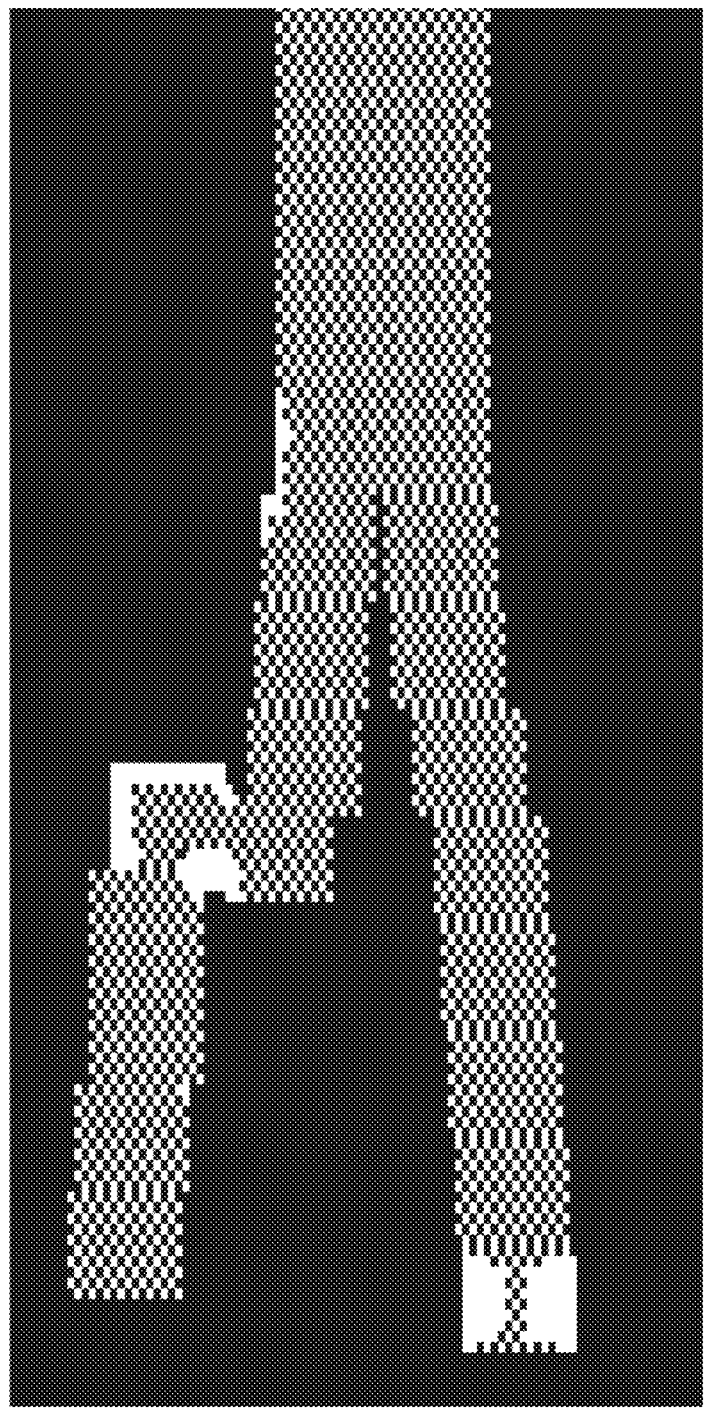
FIG. 3 is a schematic diagram of X-ray CT image information on a lesion in each of left and right arteries of lower limbs in artery to which the left lower limb artery and the right lower limb artery are connected from an aorta through an aortailiac bifurcation of the diagnostic method according to the embodiment.

A virtual X-ray CT contrast image illustrated in FIG. 3 is a virtual X-ray 3D-CT image imaged using an X-ray 3D-CT multislice apparatus using the same model as the X-ray angiographic image in FIG. 2. Portions having a larger X-ray contrast, for example, calcified parts having calcium (calcium phosphate), having smaller electromagnetic wave information than the body tissue appear to be shiny in white. In accordance with an exemplary embodiment, based on the detected electromagnetic wave information or the image information obtained by converting the electromagnetic wave information into images, a shape and position of aorta, blood vessels of the arm such as the radial arteries, or arteries of the lower limbs, the distances from the bifurcation of the blood vessel to the lesions, the thickness of the blood vessels, the length of the stenosis, the degree of curvature, the stenosis rate, the hardness of the lesions, and the like may be extracted as the electromagnetic wave information.

If there are lesions on both sides of the bifurcation, the distance from the bifurcation is a distance from the bifurcation to a proximal side of the lesion when assuming a vertical cross section of the blood vessel is virtually a circle and centers of the vertical cross sections of the blood vessel are connected from the center of the vertical cross section at the bifurcation in a longitudinal direction. Alternatively, the distance from the bifurcation may be evaluated by the difference subtracted from the value of each distance. Alternatively, determination may be done by the name of the blood vessel with the lesion instead of measuring the distance. Alternatively, in FIG. 13, measurement from a root corresponding to an aortailiac bifurcation 5 is also applicable.

The blood vessel diameter of the lesion is estimated intravascular diameter in the case of no lesion. Based on the image information, comparison may be achieved by measuring the inner diameter of the normal blood vessel on the distal side and the proximal side of the lesion and calculating an estimated value from an average value of the inner diameter on the distal side and the proximal side. Specifically, the blood vessel diameter may be obtained on an image acquired by using a CT image or from an intravascular image information obtained by measurement using an image diagnosis catheter. Alternatively, an extravascular diameter of the lesion may be used.

In accordance with an exemplary embodiment, the stenosis rate can be expressed by the inner diameter (minimum lumen diameter: MLD) of the smallest lumen diameter of the blood vessel in the lesion site and the stenosis rate calculated from an estimated blood vessel diameter (RD) when there is no stenosis in the stenosed site as shown in Equation (1).

$$\% \, DS = (1 - MLD/RD) \times 100 \tag{1}$$

In accordance with an exemplary embodiment, the stenosis rate can be measured and compared based on the image information. For example, the blood vessel diameter may be obtained on an image acquired by using a CT image or from an intravascular image information obtained by measurement using an image diagnosis catheter.

The length of the lesion refers to the length of the lesion from the proximal part of the lesion to the distal part of the lesion. The length of the lesion can be measured and compared based on image information. For example, the length of the lesion may be determined on an image acquired using a CT image or angiographic image or determined from intravascular image information obtained by measurement using an image diagnosis catheter.

As used herein the term "curvature" is intended to mean a magnitude of curvature or bent calculated at each curved or bent portion at a center line of the blood vessel, and may be expressed by using a curvature factor or a radius of curvature. The curvature can be calculated by the following method. A center line of the blood vessel is derived by calculating center points of blood vessels based on the image information on blood vessels and connecting the center points at a plurality of points in the blood vessel with the lesion. Note that the "center of blood vessel" means the center of an area surrounded by a vascular wall in a transverse cross-section of a blood vessel. The curvature may be evaluated by the minimum curvature radius of the lesion.

In accordance with an exemplary embodiment, the hardness may be determined such that if chronic total occlusion (CTO) occurs, the proximal side can be harder because of being always exposed to the blood flow and the peripheral side can be softer than the proximal side because the amount of blood flow is relatively small, and may be determined from the intravascular image information such as IVUS or OCT. Instead of the image, data obtained by direct measurement using a guide wire with a sensor may be used, and a distal end load of the guide wire that can pass through the lesion at that time may also be used.

For calcification in terms of the hardness, a CT value (HU: Housfield unit) may be used as the degree of X-ray absorption in a case of using X-ray CT images.

In the CT image, a 2 dimensional (two-dimensional) image "pixels" or 3 dimensions (three-dimensions) are assigned a black and white tint value (image density value) assigned to a cube "voxel" to represent a CT image. In accordance with an exemplary embodiment, this image density value is referred to as "CT value" in (medical professional) CT, and the CT value can be expressed as −1000, which is the lowest value of empty air, as the origin of water at 0. Then, if the air −1000 is set to be black on a CT image, the calcium absorbing a larger amount of X-rays than water and air becomes white. Therefore, the calcification lesion due to calcium deposition has a higher CT value and thus gleams in white with higher brightness. Therefore, the calcification lesion (i.e., white part) may be diagnosed as being harder than the black lesion.

In this embodiment, treating the lesion proximal to the bifurcation first is selected through diagnosis based on the distance information from the bifurcation to the lesion out of the image information.

In accordance with an exemplary embodiment, the reason for selecting the information on the distance from the bifurcation is to determine the length of the catheter and the guide wire to be used first. If the catheter does not reach a target position, treatment cannot be achieved, and use of a new catheter will be required. Alternatively, there may be a case where continuous treatment cannot be performed.

For example, continuous treatment may not be able to be performed since the distance of TRI from the puncture site to the lesion for the lower limb artery is longer than that of TFI and TBI for lower limb arteries, and because there is a case where the distance from the puncture site to the bifurcation for the right TRI is longer than the left TRI by approximately 10 cm to 20 cm for passing through the brachiocephalic artery and thus a longer catheter may be needed. In accordance with an exemplary embodiment, the bifurcations include at least, in the case of the lower limbs, three bifurcations; the aortailiac bifurcation, the bifurcation between the external iliac artery and the internal iliac artery each of the left and right legs, the bifurcation between the superficial femoral artery and the deep femoral artery, and the popliteal artery, and alternatively, the collateral circulation and the more peripheral bifurcations are also applicable.

Furthermore, diagnosis to determine the lesion to be treated first may be made based on information that the lesion is proximal to the bifurcation.

In accordance with an exemplary embodiment, the reason why the lesion proximal to the bifurcation is determined to be treated first through diagnosis is that treatment can be started before the catheter remains bent because the time required for reaching the lesion can be shortened (or reduced).

When the treatment of the lesion proximal to the bifurcation is terminated rather easily in a relatively short time, the surgeon and the patient do not feel fatigue, and thus the surgeon can further maintain concentration, for example, on a time-consuming treatment of a lesion distal to the bifurcation, which may require additional time to reach the lesion distal to the bifurcation.

In the same manner, since the fatigue of the catheter can be reduced, and thus a guide wire can pass rather easily through a true lumen (i.e., actual intima-lined artery) even in meandering lower limb blood vessels which can be difficult to pass, treatment can be achieved rather easily and in a relatively short time.

In contrast, when the lesion distal to the bifurcation is treated first, the catheter may be significantly deformed, and the lesion proximal to the bifurcation, which is normally easier to treat, may not be treated, and costs may be increased by having to replace the catheter.

The information that the corresponding lesion is proximal to the bifurcation may be determined by a blood vessel having a lesion, regardless of the information on a distance that may be measured from the image information. For example, in the case where a first lesion (lesion L1) in the right common iliac artery of the right lower limb artery and a second lesion (lesion L2) in the left superficial femoral artery of the left lower limb artery are present, it may be determined that the first lesion (lesion L1) in the superficial femoral artery is nearer (or closer) to the puncture site.

Furthermore, diagnosis is continued to determine whether treatment of the other lesion proximal to the bifurcation is to be performed or not. If the relative burden on the patient is anticipated to be rather excessive, for example, a rather long time or excessive time is needed to treat the other lesion, the diagnosis may be to complete the procedure by performing a catheter treatment on only one side (and corresponding lesion) and performing the treatment on the other lesion on another day.

Alternatively, after the treatment of the lesion proximal to the bifurcation, when the catheter treatment is not necessary for the other lesion as a result of diagnosis, it can be determined through diagnosis that no catheter treatment is performed. In this case, diagnosis may be selected from a non-invasive treatment method, such as medication treatment or exercise therapy. In contrast, when the lesion is relatively far (i.e., at a relatively great distance) from the bifurcation and the catheter does not reach, the diagnosis may be to puncture the femoral artery near the lesion and introducing a catheter, or alternatively, for example, if the location of the lesion still presents difficultly, the diagnosis may be treatment by puncturing from the distal side of the popliteal artery regressively.

If the catheter treatment is relatively difficult, it may be switched to a bypass surgery, and if it is determined that the operation cannot be performed, for example, the diagnosis may be amputation of the lower limb.

If the distance from the bifurcation cannot be determined, for example, when the distance from the bifurcation is substantially equal, a primary diagnosis which does not determine which of the lesions is to be treated first from the information on the distance from the bifurcation, and then diagnosis may be made to determine which lesion is to be treated first based on other information on the lesions.

The expression, "the distance is equal" may include a case where measured values on the image are identical, and may include a difference in distance to an extent that does not create any substantial difference in effects of treatment and in operation time irrespective of which one of those is treated first.

Performing only diagnosis and not performing treatment on the same day is also applicable. In addition, the diagnosticians and surgeons may be different.

Embodiment of Diagnostic Method

Next, an actual procedure of diagnosis by a person without depending on artificial intelligence, which is described in (I) in FIG. 1, will be described.

A patient lying in a position on an operation table equipped with an X-ray fluoroscopic apparatus is irradiated with X-rays as electromagnetic waves, and the transmitted X-rays are detected by a flat panel detector (FPD) as electromagnetic wave information. The X-ray fluoroscopic apparatus creates an image through computation from the detected electromagnetic wave information (X-ray signal intensity).

From the image information, information on blood vessels and lesions can be acquired, and image information on an aortailiac bifurcation, blood vessels of left and right lower limb arteries, and lesions in each lower limb artery can be acquired. If necessary, information on the placement, bifurcations, length, and thickness of the blood vessels, and the lesions, for example, information on a distance from a bifurcation for the lesions, the thickness of the blood vessels where the lesions reside, the stenosis rate, the length of the stenosis, the curvature, and the hardness can be obtained.

Figure 13:
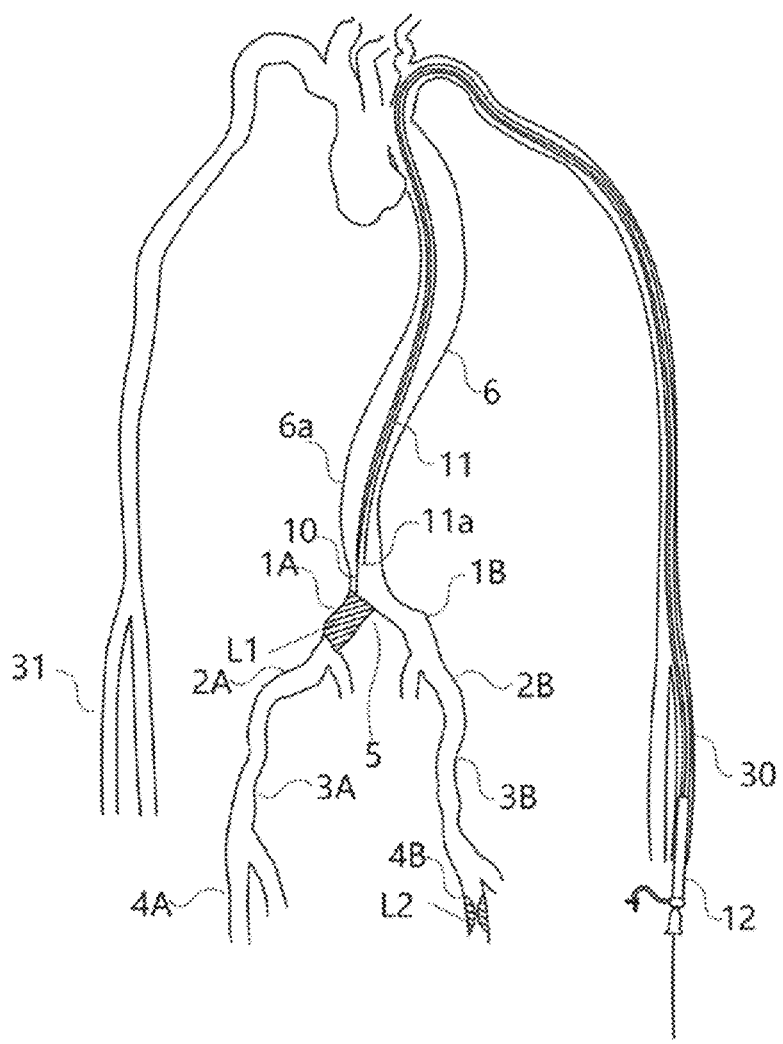
FIG. 13 is a general explanatory drawing of a lesion and a placement of a catheter in a blood vessel in a treatment method according to the embodiment.

From the image information, the occluded site L1 of the right common iliac artery in FIG. 13 is identified as a lesion distal to the bifurcation and the stenosed site L2 in the left superficial femoral artery in FIG. 13 is identified as a lesion distal to the bifurcation. Using the information on the distance from the bifurcation, the lesion to be treated first is determined. From the image information, the distance was measured on the screen, and the distance from the aortailiac bifurcation to a proximal end of L1 was 2 cm, and to a proximal portion of L2 was 25 cm. Based on this result, a diagnosis is made to determine that the first lesion (lesion L1) proximal to the bifurcation is to be treated first, followed by treatment of the second lesion (lesion L2) distal to the bifurcation.

II. Diagnostic Method Based on Artificial Intelligence

Next, a diagnostic method based on artificial intelligence shown in II in FIG. 1 will be described.

Each term is defined as follows.

Artificial intelligence (AI) is a computer system with intelligent functions, such as inference and determination, including a knowledge base part configured to accumulate knowledge, and an inference unit that derives conclusions from the accumulated knowledge, and includes those having a learning function that automatically constructs a knowledge base and corrects erroneous knowledge. As a specific example, machine-learning, artificial neural networks, expert system, case base reasoning, Bayesian network, fuzzy control, evolutionary calculation, etc. are included, and may be combined with generation of an inference rule of an expert, such as an ACT-R, through a neural network or a generation rule based on statistical learning.

Machine-learning is one of artificial intelligence and is a technology and a technique that attempt to realize a function similar to a learning ability that a human naturally performs, and also is a technique that allows a computer to learn without explicitly instructing through a program. Learning methods include supervised learning, semi-supervised learning, unsupervised learning, and reinforcement-learning.

Supervised learning is one of the learning models for machine-learning. For example, just like a teacher making a student to remember an answer (label) beforehand, labeled information is provided in advance, and a function to map the input and the corresponding output is generated. For example, in a classification problem, the generated corresponding output is referred to as a classifier, and an example expressed by input vectors and classification corresponding to outputs is provided, and a function that maps these values is approximated. If the generated corresponding output is a regression problem, it is referred to as a regression curve.

Specifically, techniques such as backpropagation, support vector machine, simple Bayes classifiers, Interactive Dichotomiser 3 (ID3), and boosting are exemplified.

Unsupervised learning is different from supervised learning in that the "things to be output" from learning models of machine-learning are not decided beforehand, and unsupervised learning can be used to extract the essential structure that exists behind the unlabeled information. Examples include cluster analysis, principal component analysis, vector quantization, self-organizing maps, and generative adversarial networks (GAN).

In accordance with an exemplary embodiment, GAN uses two ANN generators; a generator and a discriminator. The generator creates real and replica data as training data, and the discriminator identifies the real and replica and learns the difference, so that accuracy of discrimination can be enhanced, and thus each learning advances to each other. Ultimately, GAN is unsupervised learning that the generator can generate data similar to the training data used in "supervised learning".

Semi-Supervised Learning is a learning model that can use a small amount of labeled information to make use of a large amount of unlabeled information, making learning simpler. More specifically, Semi-Supervised Learning can generate an approximation function or a classifier, and Semi-Supervised Learning can refer to a bootstrap method, a graph based algorithm, and the like. Artificial Neural Network (ANN) means general learning models as a whole in which artificial neurons (nodes) forming the ANN by synaptic connection change a synaptic connection strength by learning to have a problem solving capability. The artificial neurons in general artificial neural networks make use of very simplified action of neurons in living bodies.

Although the ANN may be classified into the supervised learning which is directed to optimization with respect to the problem by inputting teacher signals (correct answers), the unsupervised learning without using the teacher signals, semi-supervised learning having intermediate features, and reinforcement-learning. The neural networks of three or more layers are proven to be differentiable and have capability of approximating any continuous arbitrary functions.

Field Forward Neural Network (hereafter referred to as FFNN) is an ANN learning model devised first and having a simple structure. FFNN is a network having no connection to be looped to the ANN, and propagating a signal only in one direction such as an input node→an intermediate node→an output node.

Convolutional Neural Networks (hereafter referred to as CNN) refer to a field forward neural network which is not totally connected.

CNN uses Neocognitron, which is devised based on neurophysiological knowledge of visual cortex of brain of organisms. Neocognitron is a learning model including convolution layers corresponding to simple type cells to perform feature extraction and pooling layers corresponding to complex cells with the function of allowing a positional displacement arranged hierarchically and alternately and using backpropagation.

The CNN includes AlexNet, as well as those using a ramp function Rectified Linear Units (ReLU), Local Response Normalization (LRN), Overlapping Pooling, Dropout, ZFNet, GoogleNet incorporating Inception Module, Global Average Pooling (GAP), addition of Auxiliary Loss, Inception-vX, VGGNet, Residual Networks (ResNet), Residual module, batch normalization, He initialization, Squeeze-and-Excitation Networks (SENet).

As an improvement on the Residual module, there is Wide ResNet, Pyramid Net.

Usage of unique modules includes ResNeXt, Xception, and Separable convolutions.

Usage of unique macro Architectures includes Residual Networks of Residual Networks (RoR), Fractal Net, Dense Net, Bottle Neck version of DenseNet, and Transition layer. For example, Dense Net is Multi-Scale Dense Net (MSD Net) which has been extended to have a feature map of multiple scales and in addition to make processing time variable depending on a difficulty level of a sample by outputting the result in the middle of the network.

In regularization, there are Stochstic Depth, Swapout, Shake-Shake Regularization, ShakeDrop, Cutout/Random Erasing, Mixup, Squeeze Net and Mobile Net that are aware of speedup.

Although the design of the model architecture has been done by hand, it is possible to design the model architecture automatically.

Recurrent Neural Network (RNN) is also referred to as Field Back Neural Network, and is a learning model in which signals are propagated in both directions, unlike FFNN. If all nodes have connection with all other nodes, it is referred to as all-to-all connected recurrent neural networks.

Diagnosis of static images that do not include time series can be done by CNN, and may be used to diagnose image information including time series, such as documenting the results of the image diagnosis of CNN by using RNN, or arranging motion images of surgical operation or historical image information side by side for comparison.

RNN can also be used for recording the results of image reading or the results of diagnosis of CNN in document, or for communicating these results to a patient in language.

For example, Bidirectional RNN, Deep RNN, Long Short-Time Memory (LSTM), and Truncated Back propagation through time can be used as types of RNN.

Figure 4:
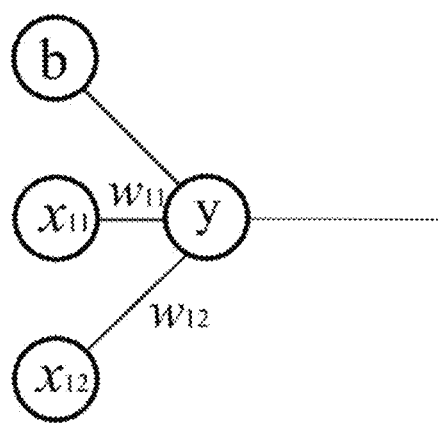
FIG. 4 is a conceptual illustration of diagnosis of a lesion to be treated first by the diagnostic method based on machine-learning according to the embodiment from information on a distance from a bifurcation using a simple perceptron.

Perceptron is composed of nodes and connection lines as illustrated in FIG. 4, and signals are transmitted by a weight and a bias. A network having two layers, that is, only an input layer and an output layer, is referred to as Simple perceptron.

In a case of the simple perceptron, where the distance $x_{11}$ distal to the bifurcation and its weight $w_{11}$, the distance $x_{12}$ proximal to the bifurcation and its weight $w_{12}$, and the bias b are expressed as Equation (2):

$$y = w_{11} \cdot x_{11} + w_{12} \cdot x_{12} + b \qquad (2)$$

For lesions L1 and L2 in FIG. 13, if y>0, it is defined that L1 is to be treated first, and if y≤0, it is defined that L2 is to be treated first. In this case, one of positive and negative signs may be changed such as $w_{11}$<0 and $w_{12}$>0.

The weight is a numerical value of the importance of the input value, and if the weight is large, the input value is deeply related to the features for learning, and in contrast, if the weight is 0 for the input value, the input value is not taken into consideration.

The update equation for the weights is given by Equation (3), where ρ is the learning rate.

$$w_i \leftarrow w_i - \rho(\partial E/\partial w_i) \qquad (3)$$

Bias is a numerical representation in perceptron indicating that treating the lesion proximal to the bifurcation first is advantageous in FIG. 13.

For example, if the effects of treatment are high by treating the lesion proximal to the bifurcation first, treating the lesion proximal to the bifurcation is represented by a positive value (b>0).

In accordance with an exemplary embodiment, the weights and biases may be set by a person, may be automatically updated by a setting initially done by a person or by input information, or may be automatically set or updated by machine-learning.

Figure 5:
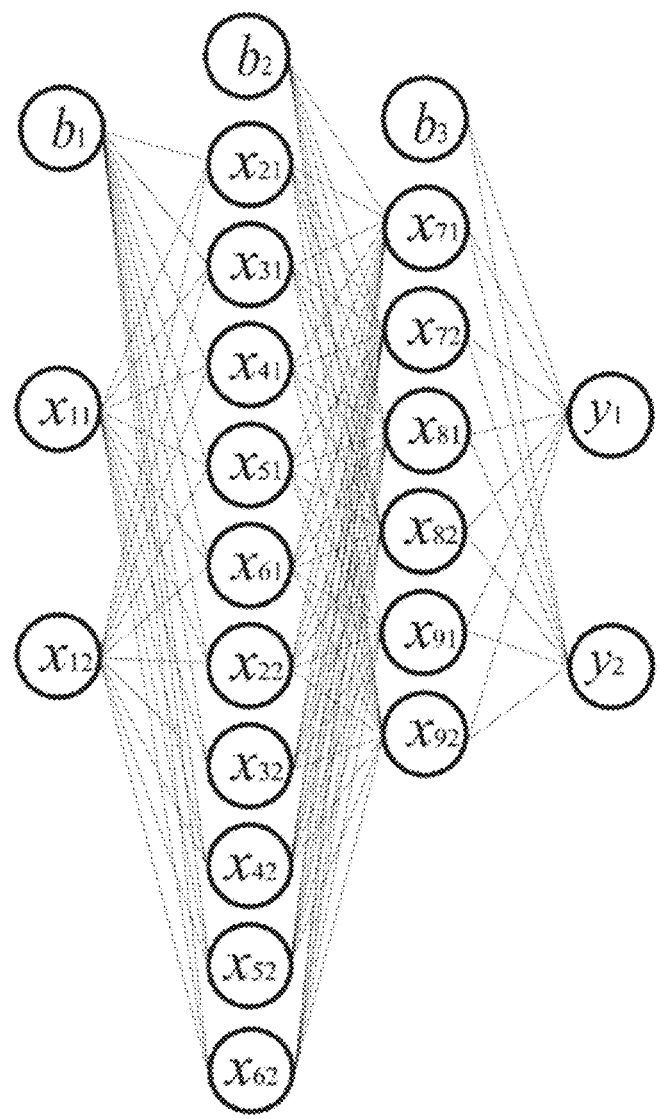
FIG. 5 is a conceptual illustration of diagnosis of a lesion to be treated first by a diagnostic method based on machine-learning according to the embodiment from information on a lesion of a patient including information on the distance from the bifurcation using a multilayer perceptron.

Multilayer perceptron (abbreviated as MLP) is a classification of a field forward neural network illustrated in FIG. 5.

This is similar to the simple perceptron in setting a bias $b_1$ that it is advantageous to set a large weight for the $x_{12}$ or to treat the lesion proximal to the bifurcation first when the distance information from the bifurcation to the lesion is extracted from the image information, and the distance from the bifurcation is $x_{11} > x_{12}$.

The distance information may be set as a first layer, and the thickness of the blood vessel $x_{21} > x_{22}$, the length of stenosis $x_{31} > x_{32}$, the curvature $x_{41} > x_{42}$, the stenosis rate $x_{51} > x_{52}$, and/or the hardness of the lesion $x_{61} > x_{62}$ (i.e., other feature quantities) can be extracted as input values and set as a second layer. The second layer is combined with the first layer which is based on the feature quantity of distance. Then, which of the lesion distal to the bifurcation and the lesion proximal to the bifurcation is to be treated first may be diagnosed.

Alternatively, diagnosis may be performed by using other image information on the patient, for example, the distance $x_{71} > x_{72}$ from the puncture sites of the left and right radial arteries to the aortailiac bifurcation, the distance $x_{81} > x_{82}$ from d-RA to the aortailiac bifurcation, and the distance $x_{91} > x_{92}$ from the s-RA to the aortailiac bifurcation as a third layer.

Using these nodes, an output $y_1$ that indicates treating the lesion distal to the bifurcation first, and an output $y_2$ that indicates treating the lesion proximal to the bifurcation first are obtained.

The output may be diagnosis saying that the lesion proximal to the bifurcation is to be treated first or may be a numerical value as probability where $y_1 + y_2$ is "1".

Figure 8:
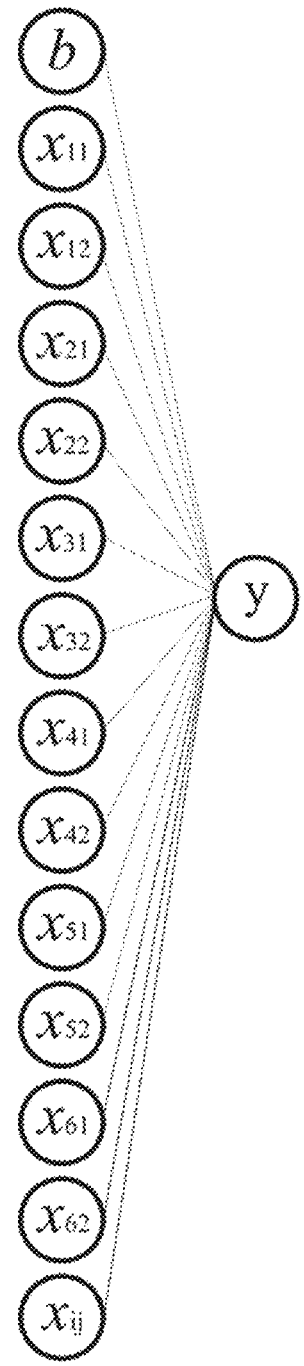
FIG. 8 is a conceptual illustration of diagnosis of a lesion to be treated first by the diagnostic method according to the embodiment from other information on a lesion of a patient including information on the distance from the bifurcation in the same layer of a simple perceptron.
Figure 9:
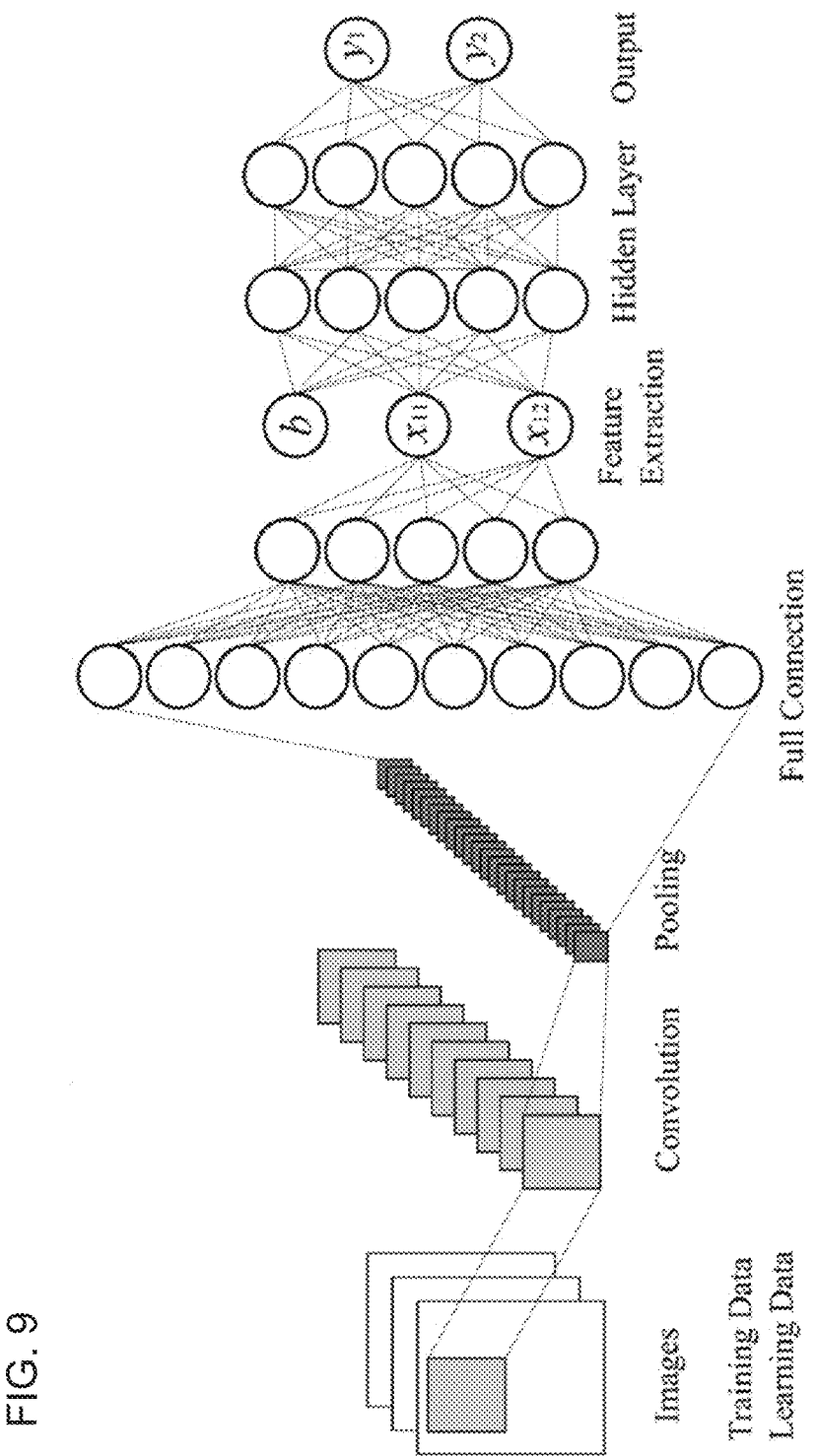
FIG. 9 is a conceptual illustration of the diagnostic method according to the embodiment performing image information based on a convolutional neural network (CNN) and diagnosing a lesion to be treated first by deep-learning using information from a lesion of a patient including extracted information on the distance from the bifurcation.
Figure 10:
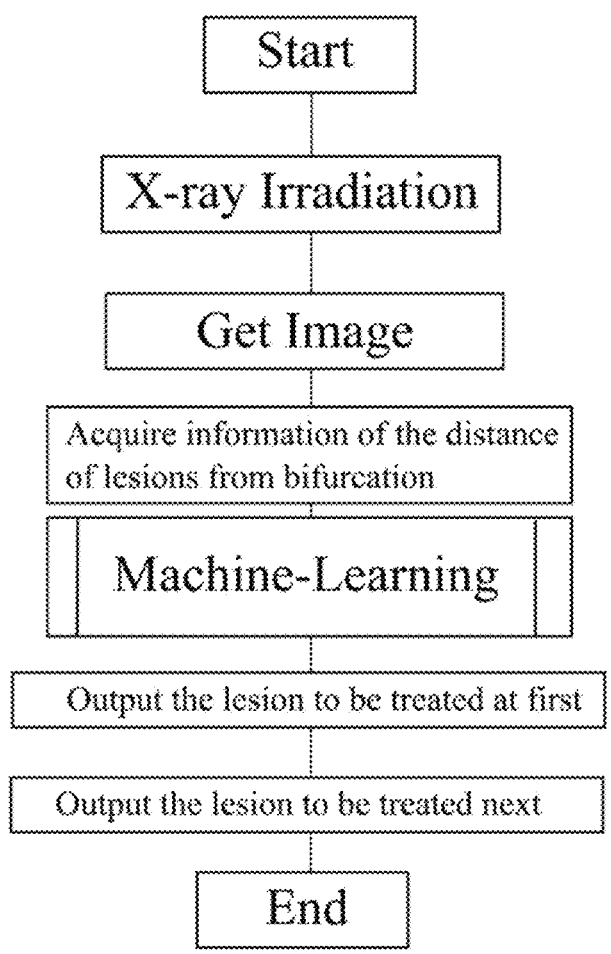
FIG. 10 is a conceptual illustration of diagnosis based on machine-learning according to the embodiment.
Figure 11:
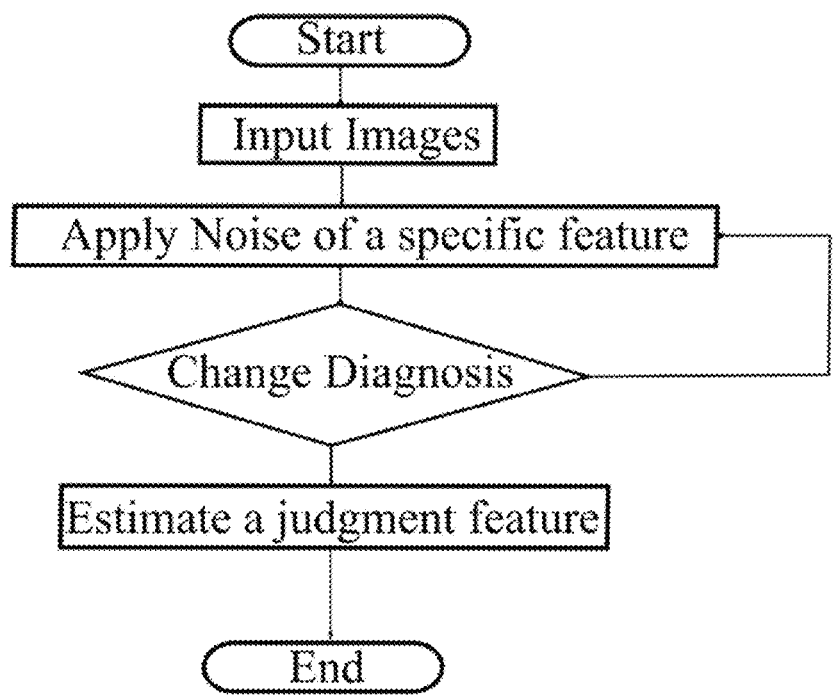
FIG. 11 is a conceptual illustration of a method for validation of the diagnosis based on machine-learning according to the embodiment.

As illustrated in FIG. 8, the information relating to the distance may be set to have nodes in the same layer. However, when the determination cannot be made only from the distances from the bifurcation to the lesions, it is preferable to provide the distance information from the bifurcation to the lesions and other information on the lesions are set in different layer because more patterns of learning model are obtained as illustrated in FIG. 9.

MLP consists of layers having at least three node layers. Except for the input nodes, an individual node is a neuron that uses a nonlinear activation function. MLP uses a supervised learning method called error reverse propagation (back propagation) method for learning. The multilayered structure and nonlinear activation function distinguish the MLP from the linear perceptron. MLP can identify information that is not linearly separable.

Overlearning or overfitting refers to a state that has been learned for training data but not to be fit and generalized for unknown data (test data) in statistics or machine-learning.

Figure 7:
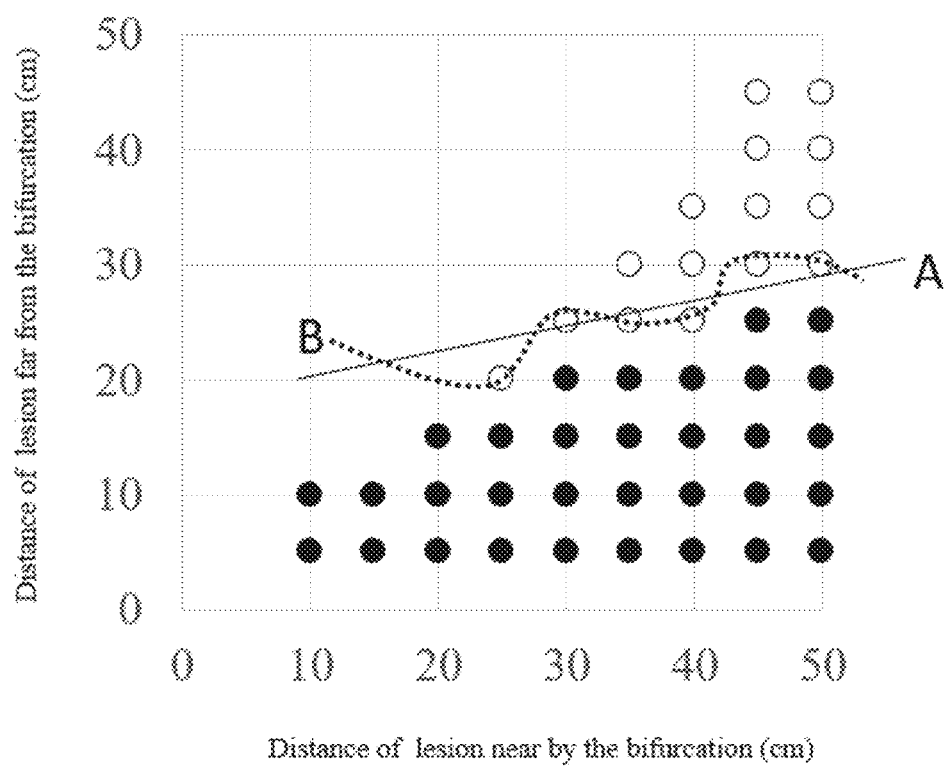
FIG. 7 is a graph showing a borderline reason for diagnosis of a lesion to be treated first by the diagnostic method according to the embodiment from information on a lesion of a patient including information on the distance from the bifurcation using a support vector machine.

In FIG. 7, if the training data is not typical, such as line B, the learning also fits a particular random (independent of the characteristic to be learned originally) feature of the training data. While the performance of training data is improved in such a process of overfitting, the results of other data can be adversely affected. Overtraining is also referred to as a process of overfitting in ANN training, which may prevent overlearning by regularization or dropout.

One of the reasons is that the model can be more complex and too flexible compared to the number of training data, such as too many parameters for fitting a statistical model. Unreasonable and incorrect models can be fully fit if they are too complex compared to the available data.

A node is a nodal point in a perceptron that corresponds to a neuron in a human brain.

The node includes an input node, an output node, and an intermediate node with activation functions that are output to input.

Ensemble learning is a technique of machine-learning that combines a plurality of learners learned individually to enhance generalization ability, and a random forest is a method using ensemble learning to average the results of a plurality of decision trees.

Dropout is a kind of regularization that prevents overlearning of the neural networks while ignoring randomly some parts of neurons (dimensions) and is a kind of regularization that advances learning while ignoring the neurons at a constant probability.

Even without increasing the input data, the significance of the solution may be enhanced by reducing the dimensions, so that the reliability can be improved by parallelizing identifiers irrespective of low detection rate.

Regularization is a method of introducing additional terms in mathematics and statistics to prevent overlearning in machine-learning and to solve ill-posed problems in inverse problems. Regularization is introduced to penalize the complexity of the model, and may provide a penalty to the norm (vector length) of the parameter.

Decision tree is a predictive model in the field of machine-learning, which leads to conclusions regarding the target value of a subject from the result of observations on a subject. An internal node corresponds to a variable, and a branch to a child node indicates a possible value for that variable. The leaf (end point) represents the predicted value of the target variable for a variable value represented by a route from the root. A decision tree is a mathematical technique and calculation method that represents, classifies, and generalizes data sets, and the data is expressed by Equation (4) shown below.

$$(x,y) = (x_{11}, x_{12}, x_{21}, x_{22}, x_{31}, x_{32}, \ldots, x_{k1}, x_{k2}, y) \quad (4)$$

Figure 6:
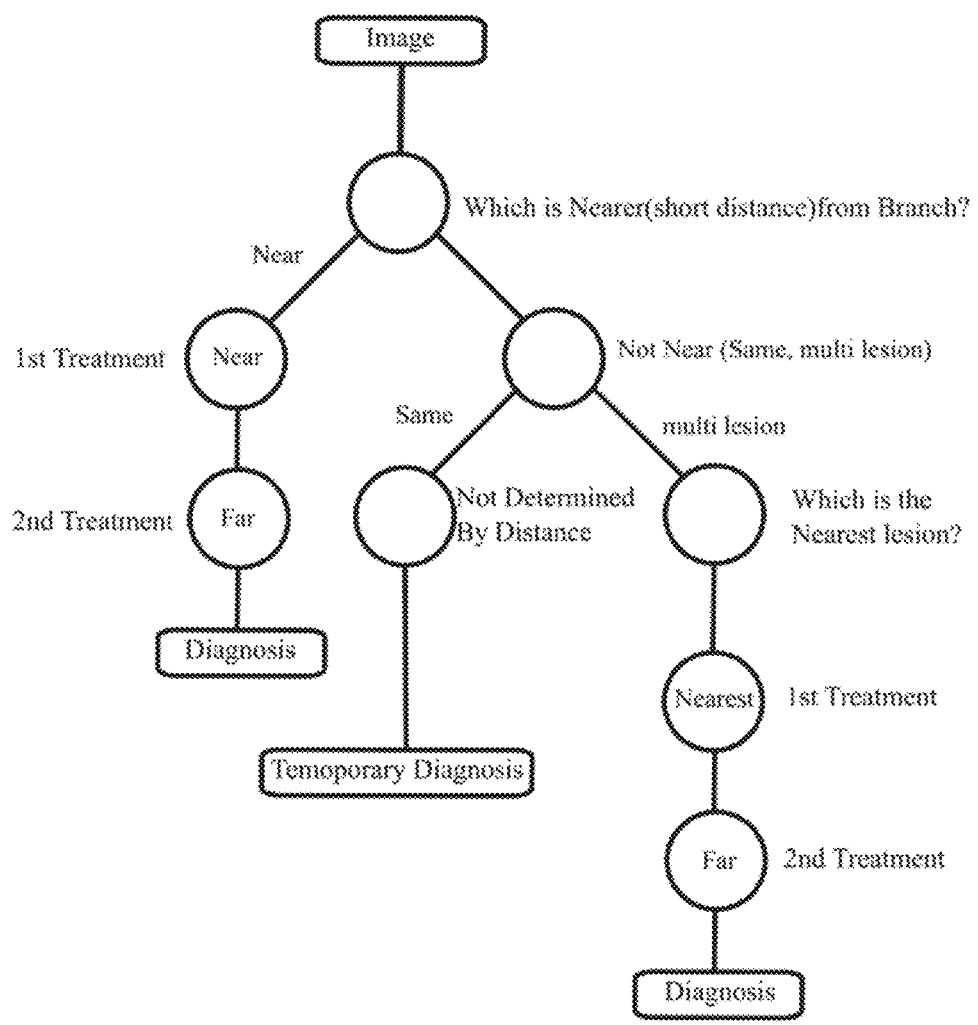
FIG. 6 is a conceptual illustration of diagnosis of a lesion to be treated first by the diagnostic method according to the embodiment from information on a lesion of a patient including information on the distance from the bifurcation using a decision tree.

The output y is an object for understanding classification or generalization, and the remaining variables $x_{11}$ and $x_{12}$ are used for approximation of the function. A regression tree (estimate of duration (or stay) of hospitalization of a patient) or classification tree (classification tree), if y is a classification variable, is used for "decision making for determining which one of the lesion distal to the bifurcation and the lesion proximal thereto is to be treated first" as shown in FIG. 6, for example.

Random forest (or randomized trees) is an algorithm for machine-learning proposed by Leo Breiman in 2001.

A plurality of sub-samples are generated by random sampling from observation data to be learned (bootstrap samples), the sub-samples are used as training data, the same number of decision trees are created, and nodes are created until the specified number of nodes $n_{min}$ is reached.

The creation of nodes is achieved by selecting some of explanatory variables of the training data, and then determining a split function of the nodes by using an explanatory variable that best classifies the training data and a threshold value associated with the explanatory variable that best classifies the training data.

Specifically, the creation of nodes corresponds to creating a group of decision trees having a low correlation by using randomly sampled training data and randomly selected explanatory variables, and the final output can be determined as follows.

Regarding the classification problem, classification may be based on majority voting when the output of the decision trees is classes, and based on the class having the highest average value in the case of stochastic distribution. Regarding the regression problem, average value of the outputs of the decision trees may be obtained.

Principal Component Analysis (PCA) is a method of reducing a dimension by synthesizing a new index that approximates the distribution of information as a whole. For example, six elements: "distance from a bifurcation", "stenosis rate", "length of stenosis", "curvature", "thickness", and "hardness" are multiplied (directly) to synthesize two indexes of "accessibility" and "penetration", and six dimensions are reduced to 2 dimensions (two-dimensions) to enable simplification of the classification and improvement of calculation speed.

This synthesized indicator is referred to as "main component". When the accessibility is a function of the distance from the bifurcation, if diagnosed by reachability, it may be considered that diagnosis is done based on at least by the information on the distance from the bifurcation.

Reinforcement-learning is a method to learn how to act by observing a surrounding environment. Action absolutely affects the environment, and feedback is returned from the environment in the form of remuneration, which becomes a guide of learning algorithm. For example, reinforcement-learning can be performed by the Monte Carlo method, Q-Learning, SRASA, Actor-CD, DQN, Dueling DQN, Prioritized experience replay, UNREAL, and A3C.

Artificial nerve or artificial neuron is the basic unit which constitutes ANN that is devised with reference to a biological nerve in the artificial intelligence. Artificial nerve receives one or more inputs (equivalent to one or more dendrites) and generates an output (synapse) from the sum of the inputs. Typically, the sum of the nodes is weighted and passed to a nonlinear function referred to as an activation function or a transfer function.

Deep learning is machine-learning having a multilayer perceptron having at least an input layer and an intermediate layer of one or more layers and an output layer (machine-learning that is referred to as a deep neural network).

Neural networks refer to general learning models in which artificial neurons (nodes) that form ANN by connecting synapses alter the connection strength of synapses by learning and have a problem-solving ability. Artificial neurons in general ANN use neurons of a living body, which is simplified in the extreme in operation.

The neural network is divided into supervised learning which is optimized to the problem by inputting labeled information (correct answer), unsupervised learning without using labeled information, and semi-supervised learning and reinforcement-learning, and a neural network with three layers or more can be approximate a continuous arbitrary function by differentiability.

Feature quantity is a measurable property of the object to be analyzed, and if the lesion is in a bifurcated blood vessel connected via the bifurcation, and means, for the lesions having the bifurcation, a distance from a bifurcation, the thickness of a blood vessel, the stenosis rate, the length of the stenosis, the degree of curvature, or the hardness, but may also be a new characteristic created by machine-learning.

For example, by using the sum of the distance from the bifurcation and the length of the stenosis, a feature quantity may be generated by determining the length of penetration from the bifurcation to the terminal end of the lesion to be the distance from the bifurcation to the lesion by using the sum of the distance from the bifurcation and the length of stenosis, and also a new feature quantity may be generated from a plurality of feature quantity based on the principal component analysis.

Back Propagation (error reverse propagation) method is an algorithm used when learning a neural network in machine-learning. More specifically, the back propagation is a learning method in which, the combined load between the layers is corrected when learning data is given so that the output of the multilayer perceptron matches the learning data. The multilayer perceptron performs supervised learning by error reverse propagation method, and is used, for example, for pattern identification, and approximation of functions.

Explanation refers to extracting information underlying in weight and learned from the weight in a form that a person can understand in order to learn the feature itself in the information in the course of learning. In deep learning, the concealing problem of image classification arises. In diagnosis in medical care, explanation is considered essential from the viewpoint of informed consent.

Restricted Boltzmann Machine (RBM), which was developed by Geoffrey Hinton and Terry Sejnowski in 1985, is Boltzmann machine that does not have connections in the same layer in the stochastic recurrent neural networks among Boltzmann machines.

The learning of Boltzmann machines is impractical because when the number of inputs is n, n times of exponential time are necessary. In contrast, the restricted Boltzmann machine defines a hidden variable, and is a generative stochastic ANN which provides the stochastic distribution on the input set.

Contrastive Divergence method, which allows efficient calculation, may also be used because the connection in the same layer is not allowed.

Cross-validation refers to a method of dividing sample data in statistics, analyzing some of data first, testing the analysis for the remaining data, and validating and verifying the validity of the analysis. This is a method of validating and verifying how much the data analysis (and derived estimation and statistical prediction) can actually cope with the population.

Specifically, the cross-validation is a method of dividing the entire data of the image information into learning data and test data, and confirming the accuracy of the model, for example, when there are 100 pieces of data as a whole, dividing the data at a ratio of 6 to 4, and dividing the learning data into 60 pieces and the test data into 40 pieces for learning. In accordance with an exemplary embodiment, hold out method is preferable if the number of data is 100000 or more pieces.

K-fold cross-validation divides the entire data into K, one of which is the test data, and the remaining K−1 piece is decomposed into training data.

Thereafter, the test data and the learning data are exchanged, and validating all the cases repeatedly so that all the cases become the test data.

In other words, data divided into K is validated by K times, and the accuracy of the model is verified by averaging the results obtained in this manner. In accordance with an exemplary embodiment, this validation is suitable for a case where the number of data is not more than 1000 pieces, and can be used if the number of data is not larger than 10000 pieces.

Leave-one-out cross-validation (LOOCV) extracts only one case from a sample group as test data, and determines remaining cases to be the learning data. This validation is repeated until every case becomes the test data once. This is the same as the case where K of K-division cross-validation is made to be the sample size.

Contrastive Divergence Method (CD Method) is a method to reduce the amount of calculation significantly by approximating an expected value for obtaining the gradient of parameter in order to approximate the stochastic distribution expressed by RBM to the true distribution.

In the CD method, sampling is performed by k times to approximate the second term of the gradient obtained previously with the expected value, and preferably, a method of performing sampling only once is commonly used.

Activation function, also referred to as transfer function, is a function that is applied after linear transformation in ANN, which corresponds to a nonlinear function such as a ramp function or a sigmoid curve, or a constant function like $f(x)=x$.

Ramp function (ReLU function ramp function) is a real function of a variable, which is a piecewise linear function that is easily obtained as an average of independent variables and their absolute values, and is represented by Equation (5).

$$R(x) = \begin{cases} x, & x \geq 0 \\ 0, & x < 0 \end{cases} \quad (5)$$

The sigmoidal curve is a model of the properties of living organism's nerve cells, and it is a real function that provides outputs other than 1 and 0. Where a is the gain and e is the base of the natural logarithm (2.718 . . . ).

$$\varsigma a(x) = \frac{1}{1+e^{-ax}} = \frac{\tanh(ax/2)+1}{2} \quad (6)$$

Loss function is a function which is equivalent to an error function as shown in Equation (7) for calculating how much extent the ANN does not match the labeled data. The loss function is an indicator of bad performance of neural network. The goal of machine-learning is to approximate this value to 0, and a hinge loss function, ε tolerance error function, Huber function, and an exponential loss function are preferred, but in Deep Learning, cross entropy error or root error are preferable.

$$\nabla E = \frac{\partial E}{\partial w} = \left[\frac{\partial E}{\partial w_1} \cdots \frac{\partial E}{\partial w_M}\right]^T \quad (7)$$

$$w^{(t+1)} = w^t - \varepsilon \nabla E$$

Gradient Descent Method is a method of calculating a local minimum value of an objective function by iterative calculation, and is used to minimize a loss function E (w) of a forward propagation type ANN. The Equation (7) is renewed from any initial value $w^{(0)}$ as the starting point, $w^{(t)}$.

The steepest gradient method, stochastic gradient descent (SGD) method, Momentum method, AdaGrad method, or Adam method may be used.

A vector has a size and a direction. In numerical n-dimensional arrays, one-dimensional array is referred to as a vector, a two-dimensional array is referred to as a matrix, and collectively, referred to as a tensor.

Hyperparameter is a parameter that can be set by a person such as a learning rate, and is different from the weight or bias that can be automated.

Support vector machine (SVM), which is a supervised machine-learning model for pattern identification published by AT&T's V. Vapnik in about 1995, is especially superior in advantages being free from the problem of local convergence, and in pattern identification capabilities such as two group classification by margin maximization and kernel trick.

For example, when the previously treated image information is used, the fact that the left and right lower limb arteries respectively have lesions and, regarding the right lower limb artery and the left lower limb artery, distance information from an aorta bifurcation and the lesion treated first are also input.

In FIG. 7, black circles indicate a case where the lesion proximal to the bifurcation is diagnosed to be treated first, and the hollow circles indicate a case where the lesion distal to the bifurcation is diagnosed to be treated first. The horizontal axis indicates the distance from the bifurcation to the lesion proximal to the bifurcation quantified into one value (scalar value) in numerical value, and the vertical axis indicates the quantified distance to the lesion distal to the bifurcation in the same manner.

The feature quantity of the lower limb artery lesion is not limited to the distance from the bifurcation, but here, it is assumed to input 2 types of 2-dimensional (two-dimensional) information in a simple manner.

When diagnosis is performed and determines that the lesion proximal to the bifurcation, right lower limb artery is to be treated first, a value of 1 indicating that the lesion is proximal to the bifurcation is given (learning data having a value of 1 is referred to as a positive example), and when the left lower limb artery is treated first, a value of −1 indicating that the corresponding lesion is distal to the bifurcation is given (similarly referred to as a negative example).

Pattern identification machine learning draws a straight line A, such as y=ax+b, on the figure based on the learning data with a positive or negative value. Then, pattern identification is intended to answer "which one of the lesion distal to the bifurcation and the lesion proximal to the bifurcation is to be treated first" when information that is not learning data (positive or negative is not taught, here, only the distances from the bifurcation on the left and the right) is input.

Margin maximization refers to a method in which the maximum generalization ability is expected on an identification line drawn so that the margin is maximized, and as used herein the term "margin" is intended to indicate the distances between the identification line and two classes according to the learning data in classification.

Threshold value is a value representing the magnitude of input or stimulus necessary to cause a certain phenomenon, and only 1 or 0 can be selected as a value of for a step function. However, real numbers can be used as a threshold value for a sigmoid function.

Informed consent is a concept that means an "agreement after sufficient information is given (communicated)".

Embodiment of Diagnostic Method Using Artificial Intelligence

Among diagnostic methods using artificial intelligence, II. Diagnosis method based on machine-learning in FIG. 1 will be described.

In the related art, a routine procedure or a more speedy procedure is achieved with certainty by converting implicit knowledge accumulated in the brain, which has been determined by human rule and sense, into explicit knowledge specific acquisition information that can be transmitted to a third party on paper or an electronic medium knowledge.

In a case where one or more lesions L1 and L2 are present in bifurcated blood vessels according to patient information acquired through diagnosis, respective distances from a bifurcation of a lesion are expressed by $x_{11}$ and $x_{12}$, their respective weightings are expressed by $w_{11}$ and $w_{12}$, and output is expressed by y. ANN, which simulates a neuron, makes the neuron to output a signal when an expression weighted for a plurality of inputs per node exceeds a threshold value, and shuts off if it does not exceed a threshold value.

In the case of a simple perceptron, it is defined that if y>0 by using the equation (2), L1 is treated first, and if y≤0, L2 is treated first. In this case, signs of positive and negative of $w_{11}$ and $w_{12}$ may be changed. Sign b represents a bias which is a numerical value indicating that treating the lesion proximal to the bifurcation first can be advantageous.

Weights and biases may be set by a person from an empirical rule of thumb as appropriate, or numerical values of the weights and biases may be obtained statistically by a large-scaled clinical trial, but become parameters to be automatically set in case of machine-learning.

Alternatively, decision may be made such that determination is not to be made by the distance from the bifurcation if y=0, or determination is not to be made by the distance from the bifurcation in a range of a<y<b.

Alternatively, if there is a plurality of lesions in one blood vessel, the distance to the proximal end of the lesion the most proximal to the bifurcation among the plurality of lesions in the one blood vessel may be newly extracted as a feature quantity.

In accordance with an embodiment, when determination cannot be made based on the distance from the bifurcation in either of the above-described cases, determination of the primary diagnosis is that which of the bifurcated blood vessels is to be treated first is not found from the distance from the bifurcation.

If the primary diagnosis is made such that determination cannot be made only by the distance from the bifurcation, the result may be displayed and the diagnosis is completed, and the result may be displayed on Graphic User Interface (GUI).

The feature quantity may be newly created by machine-learning.

Alternatively, new one feature quantity may be created based on the principal component analysis from the information on the distance from the bifurcation, and then diagnosis for determining which one of the lesion proximal to the bifurcation and the lesion proximal to the bifurcation is to be treated first may be performed based on the new feature quantity as a function of distance from the bifurcation.

When the decision trees in FIG. 6 are used to first attempt the determination only by a distance from a bifurcation but determination cannot be made from the distance from the bifurcation, the primary diagnosis such that the determination cannot be made based on the information on the distance from the bifurcation may be made, and if determination cannot be made, diagnosis may be performed by using other feature quantity.

When the decision trees are used as a random forest, diagnose may be performed to determine which one of the lesions distal to the bifurcation and the lesion proximal to the bifurcation is to be treated first in association with the primary diagnose based on the feature quantity of distance by using input values of the blood vessel thickness $x_{21}$ and $x_{22}$, the stenosis rate $x_{31}$ and $x_{32}$, the stenosis length $x_{41}$ and $x_{42}$, the curvature $x_{51}$ and $x_{52}$, and the hardness of the lesion $x_{61}$ and $x_{62}$.

Alternatively, information may be other image information other than the patient's lesion, for example, image information on patient's current state such as meandering of an entire blood vessel, especially a loop of an arm artery that is particularly difficult to pass, a history of a past surgery, presence or absence of a stent, or image information stored in the past, patient's character information written on a medical record such as patient's age, pre-existing disorders, for example, or symptoms or appearance such that the patient cannot be endure to take the same position for a long time due to lumber pain or articular pain, or even other patient's information based on a medical interview.

Alternatively, nonclinical information such as patient's requests such as reducing the duration of hospitalization, and hospital-side requests such as cost and cost-effectiveness to reduce treatment costs or labor costs may be used as other patient's information.

The patient information may be integrated into the same layer in parallel as a simple perceptron including the distance information from a bifurcation to a lesion as illustrated in FIG. 8, and information on another lesions. In this case, the weight of information of the lesion of the distance from the bifurcation may be increased. When determination cannot be made only from the distance information from the bifurcation to the lesion, diagnosis may be performed by using the information on the other lesions of the patient, for example, distances $x_{71}$ and $x_{72}$ from puncture sites of left and right radial arteries to an aortailiac bifurcation, distances $x_{81}$ and $x_{82}$ from d-RA to the aortailiac bifurcation, and distances $x_{91}$ and $x_{92}$ from s-RA to the aortailiac bifurcation.

Although the information on these distances may be provided by arranging nodes in the same layer, it is preferable to provide the nodes in different layers as illustrated in FIG. 9 because the pattern of a learning model be expanded when the distance from the bifurcation to the lesion cannot be determined only by the distance from the node to the lesion.

Specifically, in a case of a multilayer perceptron as illustrated in FIG. 9, deep learning may be diagnosed by receiving an output value from the lesion information and providing a separate layer to diagnose based on patient's information other than the information on the lesion as a stacked autoencoder.

When a person diagnoses, X-rays transmitted by X-ray irradiation are detected by FPD, and the information is acquired. The information is digitized, and the image information converted by Fourier transform and filtering is determined by a human eye.

The obtained electromagnetic wave information, for example, may be have 16 gradation tones, more preferably at least 256 gradation tones, depending on the concentration of white in the case of X-ray imaging photographs in a pixel unit.

Note that if the image information has intensity fluctuation due to overlap of blood vessels depending on a direction of imaging, the blood vessel may be separated by changing the direction of imaging, or a plurality of images may be used for machine-learning.

When the lesion is extracted as a feature quantity, the feature quantity may be determined by an analysis of a guideline such as TASC II or big data. However, any unknown information or information unrecognized as images that can be extracted as the feature quantity of machine-learning and used for determination may be used.

The feature quantity that may change determination of the lesion to be treated first can be preferable because they are recognized as important feature quantity.

Alternatively, the apparent distance on a screen from the bifurcation for determining the position of the lesion is applicable, and a name of the blood vessel may also be applicable. If the name of the blood vessel is used, RNN can be preferred to CNN.

The bifurcation may be, in the case of the TRI approach, a bifurcation between an aortailiac bifurcation and left and right lower limb arteries, the bifurcation between an external iliac artery and an internal iliac artery, the bifurcation between a superficial femoral artery and a deep femoral artery, or the more peripheral blood vessel bifurcation.

Alternatively, it may be a bifurcation between a principal vessel and a collateral circulation, or the bifurcation between an aorta and a superior mesenteric artery, an inferior mesenteric artery, a celiac artery, and also the bifurcations of the blood vessels connected to other organs or their peripheral blood vessels.

Other organs include liver, intestinal tract, spleen, pancreas, testicle, uterus, brain, kidney, and specifically, the lower limb artery, the celiac artery, the superior mesenteric artery, and the inferior mesenteric artery are preferable because a method of advancement of a catheter is the same as a blood flow and thus turbulent less likely occurs when introduced by TRI. For example, considering the liver, the TRI is preferred because the direction of orientation of the blood vessel is the same as the direction of advancement of the catheter compared to the TFI having to engage the celiac artery with a complex shape such as Shephered hook.

Next, the feature quantity for determination is selected. The feature quantity includes numerical values referred to as feature quantity quantitatively expressing features of analytic information, and includes the distance from the bifurcation to the lesion, the thickness of the blood vessel, the stenosis rate, the length of stenosis, the hardness, and the curvature.

Alternatively, a learning model may be created by a person setting feature quantity, incorporating the feature quantity and feeding the image into machine-learning.

Alternatively, the set value may be changed from an outcome of the treatment or long-term prognosis, or the outcome of the treatment may be digitized, and the value may be automatically corrected by enhanced deep learning as remuneration.

Note that machine-learning may use image information as in the case of a person, but may use non-image information that cannot be determined by a human eye if it can be recognized and classified as a feature quantity (the distance from the bifurcation).

As used herein the term "image information" is intended to include information that can be recognized, understood, or used for diagnosis by human eyes, and which is an image converted by electromagnetic wave information.

Therefore, the non-image information means information that cannot be used for diagnosis, such as a digital bit described by "0" and "1", data or data structure such as a quantum bit including both states of "0" and "1" superimposed with each other, or DICOM information itself not displayed on GUI, which cannot be recognized and incomprehensible by a human eye as the shape of the blood vessel or as the lesion. Alternatively, information that has resolution exceeding the resolution of a human eye, and thus cannot be seen by a human eye such as minute things that cannot be recognized by a human eye even in enlarged scales, the one cannot be separated into two points and is recognized as one point, difference of shade the gradation difference of which cannot be recognized are not used.

III. Validation Method

Next, the validation method will be described. As used herein the term "validation" is intended to include verifying the truth of a hypothesis by comparing a conclusion derived logically from a hypothesis against a result of a fact or a result of an experiment.

Specifically, a hypothesis is made such that if the lesion is determined to be located in each of the left and right lower limb arteries connected via the aortailiac bifurcation from the image information, less medical costs are expected by treating the lesion proximal to the bifurcation first. Logically, the number of the devices to be used can be reduced and hence the medical costs are decreased by treating the lesion proximal to the bifurcation first and then the lesion distal to the bifurcation, which may be difficult to reach before fatigue of catheter becomes too much or excessive. Therefore, a conclusion, that is, for example, diagnosis is made that the lesion proximal to the bifurcation is treated first.

For diagnosis, we will actually treat the treatment and match the image information after treatment to ascertain whether the hypothesis is true, taking the information on the distance from the bifurcation and the operation time into account.

The validation is preferably performed with image distance information from the bifurcation, but it may be evaluated by other image information on the lesion such as the thickness of the blood vessel, other image information after the treatment, the degree of improvement of the patient's symptoms, the long-term prognosis, for example, the existence of patency, the existence of the restenosis, and the period of time until the re-operation.

Image information on the patients themselves, or image information in the past of other people having similar symptoms may also be used, or information in academic guidelines, paper data, big data, or on cloud may also be used.

A diagnostic simulation based on diagnosis may be used by comparing image information after the treatment with a first simulation image (simulation image 1) in the case where the lesion distal to the bifurcation is treated first, a second simulation image (simulation image 2) in the case where the lesion proximal to the bifurcation is treated first, and if there is no difference between image information after the treatment or no difference in effects of treatment, information in the length of the operation time may be used.

Information on patients other than the image information may include patient's appearance, symptoms, medical interview, impressions and opinions, or validation may be performed by using character information such as medical records, the rule of thumb of a physician, the past person's or other medical record information, the literature and statistics in a large-scale clinic, etc.

When performing diagnosis by a person and in the case where the lesion proximal to is determined to be treated first from the image information, diagnosis may be performed on the basis of information on the result of treatment such that effective treatment is achieved within a prescheduled duration, that it took time more than scheduled and thus burdens were imposed on the patient, the procedure was completed in a shorter time than the scheduled time but the procedure was too costly because too many devices were used, the treatment was completed within half a scheduled time but unnecessary waiting time resulted because the preparation for the next patient was not finished in time, and so on.

It may also be based on nonclinical information such as data including the cost of medical devices such as catheters and medical supplies used, the duration of hospitalization in days, presence or absence of insurance coverage, payment to insurance companies, income and expenditure of the hospital, or the stock of available catheters, etc., whether the catheters are commercially available, or the number of surgeries per day.

In the diagnosis based on machine-learning, in addition to the above-described information, validation is performed so that people can recognize and understand which feature quantity is used for explanation of the results of diagnosis, that is, a conclusion of decision of the lesion to be treated first.

Therefore, the validation may be performed by a physician who is a surgeon, and it can be preferable to perform the test by a physician other than the operator or a plurality of physicians if the objective evaluation is performed objectively.

Alternatively, if information includes not only information on a patient's lesion but also nonclinical information such as cost-effectiveness or device cost, validation may be performed by a third party other than the physician, or even the artificial intelligence or machine-learning can support the validation or perform the validation itself.

In reinforcement-learning as remuneration for result of treatment, parameters or hyperparameters may be altered by a person by validation, or may be changed so as to be optimized automatically by machine-learning.

Furthermore, in the diagnostic method by machine-learning, if the weight and activation functions are set by a person, and the reasons for determination of diagnostic can be confirmed with the validation by a person, the validation may be performed by using the result of treatment and the result of diagnosis simulation, or nonclinical information such as cost.

However, when the number of layers of multilayer perceptron having large feature quantity is large, it becomes difficult to set the weight to be the reasons for determination by human determination. Alternatively, non-image information that cannot be recognized by a person cannot be recognized and incomprehensible by itself by a person and thus weighting by a person is not possible.

In order to do so, machine-learning to automatically generate the weights and activation functions through deep learning may be required.

However, the diagnostic method by machine-learning is a black box, so the knowledge or experience of a physician or evidence from a large-scale clinical trial is required.

Machine-learning using artificial intelligence, especially the ANN, for example, the diagnostic method based on artificial intelligence such as deep learning by restricted Boltzmann machine using the multilayer perceptron requires explanation because the physician cannot inform the patient with the reason, which goes against informed consent unless otherwise there is a medical reason.

Therefore, the validation of the machine-learning diagnosis allows the ANN to support the diagnosis by a physician or to perform diagnose, allows the physician to perform treatment based on the diagnosis, or allows the ANN to support the treatment by the physician or to perform the treatment.

A method for validating machine-learning may include creating an input that maximizes an ANN output (Activation maximization) method. For the ANN that deals with classification problems, the output is a classification probability for each category. Here, estimation of the reasons for determination may be performed by finding an input in which classification probability of a certain category is quite high, and specifying a "representative example" of the corresponding category by the ANN.

Alternatively, a method of Sensitivity Analysis for analyzing the sensitivity for the input may be used. That is, when the input feature amount has a large influence on the output, the input feature can be regarded as an important feature quantity, and the amount of change indicating which of the inputs the ANN is sensitive is examined. The amount of change can be determined by a gradient. Since the ANN learns by the gradient, ANN is well suited to an available optimization mechanism.

Alternatively, the SMOOTHGRAD may create a plurality of samples intentionally added with noise when the gradient is too sensitive, and average the results.

Alternatively, tracing the path from the output to the input reversely (Deconvolution/LRP), that is, making the ANN propagate to a certain layer, and then points other than points to be examined later are set to 0 for reverse propagation, so that the input that contributes to that location is reversely calculated.

In other words, it is possible to perform a nonlinear process equivalent to the ramp function, and perform explanation of important feature quantity by so-called guided back propagation.

The method of tracing the gradient from the desired label reversely for interpreting only the points contributed to the classification may calculate the contribution of each feature map leading up to the classification, and obtain a heat-map-like output by Grand-CAM by the reverse propagation with the weight.

Based on ensemble learning using the decision trees, if negated by the input value $x_{11}$ and $x_{12}$ in each decision tree, the amount of change until the determination changes to affirmative may be calculated, and the minimum amount of change is obtained from the calculated amounts of change, so that the amount of change for affirming the minimum cost may be obtained.

Alternatively, in order to constrain the result of learning to be predictable, that is, in order to avoid incomprehensible determination, that is, in order to prevent erroneous prediction such as determining to treat the lesion located closer due to the lack of information, constraint to make the trend "monotonous" may be applied.

Alternatively, the point of focus for the input is incorporated into a learning model as a distance from the bifurcation (Attention), and a mechanism indicating the point of focus for the input information to the learning model is introduced.

The basic approach to Attention may be to use not only the hidden layer immediately before, but also hidden layers in the past when outputting, and at that time, distribute the weight to important points.

Explanation that validates the reasons for determination and the contribution of the diagnosis may be performed by estimating the activation function that outputs the used feature quantity.

In addition, as a method of validating the "quantitativeness" of interpretation, a consistency of interpretation, namely interpretation for the input of the distance from the bifurcation, is close to interpretation of the information close to that input, and thus similar information is assumed to be explained in a similar way. The consistency of interpretation may be evaluated, for example, by examining how the interpretation changes when the input, which is an image, progressively slides.

In contrast, since the feature quantity which is considered to be important in the interpretation is also an important feature quantity for the learning model as well, the "validity" of interpretation seems to have a significant effect on the learning model when the feature quantity which is considered to be important for interpretation is removed in the interpretation. For example, the validity of interpretation may be obtained by gradually removing pixels that are considered to be important in interpretation, and measuring the degree of change in accuracy. In this case, the validity of interpretation is considered to be high if the accuracy of the classification is reduced most abruptly when the pixels are removed from the important ones.

Embodiment of Validation Method

As an embodiment of a validation method, when determination has changed by changing information on a distance from a bifurcation which is a feature quantity, it is estimated that the determination is made by using the corresponding feature quantity.

The ways of changing the distance information include a method of applying noise to electromagnetic wave information. In addition to applying noise to the entire electromagnetic wave information, in a case of an X-ray CT image in FIG. 2 for example, a method of applying a noise may include applying noise equivalent to white to a lesion of a left lower limb artery distal to a bifurcation in a direction toward the heart along a central axis of a blood vessel, applying noise equivalent to white to a lesion of a right lower limb artery proximal to the bifurcation from the bifurcation on a periphery side along the central axis of the blood vessel, and in contrast, applying a noise equivalent to black to the heart side. By plotting under varied noise conditions, activation functions can also be estimated.

Alternatively, normal noise removal filtering may be reversed. A median filter, an edge preserving filter, a Laplacian filter, sharpening, and gamma correction may be used as a moving average filter, a Gaussian smoothing filter, and a nonlinear filter.

When noise information on the distance from a bifurcation is applied, if a lesion L1 proximal to the bifurcation is in the right lower limb artery, and a lesion L2 distal to the bifurcation is in the left lower limb artery and if the lesion to be treated first is changed from the right lower limb artery to the left lower limb artery, it is estimated that which one of the lesions is determined to be treated first depending on the distance from the bifurcation, or diagnosis has been made depending on the information that the distance from the bifurcation is relatively large.

Alternatively, it may be estimated that the determination is made depending on the distance from the bifurcation when an output does not indicate which one of the lesions is to be treated first, but takes a probabilistic form indicating that, for example, the values of the outputs are changed by applying a noise to outputs of output $y_1$ which is 0.1 and $y_2$ which is 0.9, where $y_1$ is an output indicating that the lesion distal to the bifurcation and $y_2$ is an output indicating that the lesion proximal to the bifurcation is to be treated first.

In contrast, if no change occurs even when the noise is applied, it can be estimated that the distance from the bifurcation has no influence. In this case, it may be estimated that the determination is made based on other image information of the lesion, image information other than the lesion, the operation time, information of the medical record, or other nonclinical information such as a cost of a device.

Alternatively, methods such as Local Interpretable Model-agnostic Explanations (LIME) and SP-LIME methods may be used. LIME is to make an explanation prediction, and the explanation prediction means to understand why a learning model has made such a decision.

On the other hand, SP-LIME is a method for performing the explaining model, and is a method of comparing characteristics of respective learning models by a submodular optimization with a uniform standard. In LIME, when there is one predicted result, a simple classifier locally approximated only to the one predicted result is created to select a feature quantity effective for estimation from the simple classifier. Therefore, LIME is a method of keeping an approximation error within an allowable range by local approximation. These methods may be used for interpretation.

IV. Treatment Method

Treatment of a treatment method of the present disclosure based on at least one of diagnostic methods, a diagnostic method by a physician, a diagnostic method by machine-learning, a diagnostic method by machine-learning after explanation based on validation, and a diagnostic method by reinforcement-learning is performed.

As used herein the term "treatment" is intended to include healing of diseases or injuries. However, the treatment may be done by a person, supported by artificial intelligence, or done by artificial intelligence.

There may be a case where a patient has lesions in each of the left lower limb artery and the right lower limb artery. In such cases, it is desirable to treat the patient with a single operation, reducing the burden on the patient.

However, even in the same lower limb arteries, a distance from the bifurcation may be different, and effects of treatment and difficulties in treatment depend on the distance.

Shortening the time spent for the procedure depending on which of the lesions in the lower limbs on the left and right is to be treated first and efficiently using a guiding catheter or a therapeutic catheter are important for burden of patients, shortening (or reducing) time spent for the procedure, shortening (or reducing) the time of using the operating room, and reducing the number of catheters to be use, that is, in terms of medical economics.

According to the present disclosure, deformation in shape or deterioration of the catheter due to the treatment being passed through the significantly bent blood vessels can be relatively eliminated by treating the lesion proximal to the aortailiac bifurcation first in a patient with lesions in both of the left and right lower limb arteries, and relatively efficient treatment of the left and right blood vessels can be achieved by maintaining the blood vessel selectivity for the catheter for the subsequent treatment.

In addition, reduction of burden on the patient and reduction of medical costs can be achieved by achieving treatment with relative certainty by efficiently using the catheter and reducing the number of usages of the catheter, and while maintaining blood vessel selectivity and capability of passing the blocked portion of the guide wire and the catheter used for the treatment.

Furthermore, when the catheter assembly using the catheter as a guiding catheter and having the inner catheter placed in the lumen of the catheter (i.e., guiding catheter, the guiding catheter may be relatively easily placed (or positioned) near the lesion distal to the bifurcation where the placement can be relatively difficult.

Embodiment of Treatment Method

A procedure of treating a lesion proximal to a bifurcation followed by treatment of a lesion distal to the bifurcation for a patient having one each of lesion in each of left and right lower limb arteries connected to an aorta via an aortailiac bifurcation will be described.

In order to facilitate understanding of a treatment method of an embodiment, a flow of a procedure will first be described. In this treatment method, a catheter (guiding catheter in this embodiment) is introduced from an artery of an arm of the patient and a catheter tip is advanced to and is placed at least at the patient's aorta.

FIG. 13 shows a state in which a guiding catheter 11 is placed in a blood vessel of the patient with lesions in the left and right lower limbs, that is, an occluded portion (lesion) L1 which is chronic total occlusion (CTO) in a right common iliac artery 1A, and a stenosed site (lesion) L2 in a left superficial femoral artery 4B. In the placement step, for example, a puncture needle, which is not illustrated, is punctured into a left radial artery 30 and a mini guide wire (not illustrated) is placed in the blood vessel, then a introducer sheath 12 with a dilator (not illustrated) assembled to the introducer sheath 12 is inserted, the dilator and the mini guide wire are removed, and the guiding catheter 11 with a guide wire 10 assembled to the guiding catheter 11 is introduced through the introducer sheath 12.

In accordance with an exemplary embodiment, the guiding catheter 11 and the guide wire 10 have a hydrophilic lubricating coating to improve the insertion ability on a surface of the guiding catheter 11 and the guide wire 10.

The guiding catheter 11 is then directed along the guide wire 10 to at least an aorta 6 of the patient from the artery of the arm and the guiding catheter 11 is advanced into the aorta 6. Specifically, a catheter tip 11a of the guiding catheter 11 is advanced to the vicinity of an aortic iliac bifurcation 5 on the aortailiac bifurcation 5, and the catheter tip 11a is placed so as to be directed to an entry port of the right common iliac artery 1A.

Figure 14:
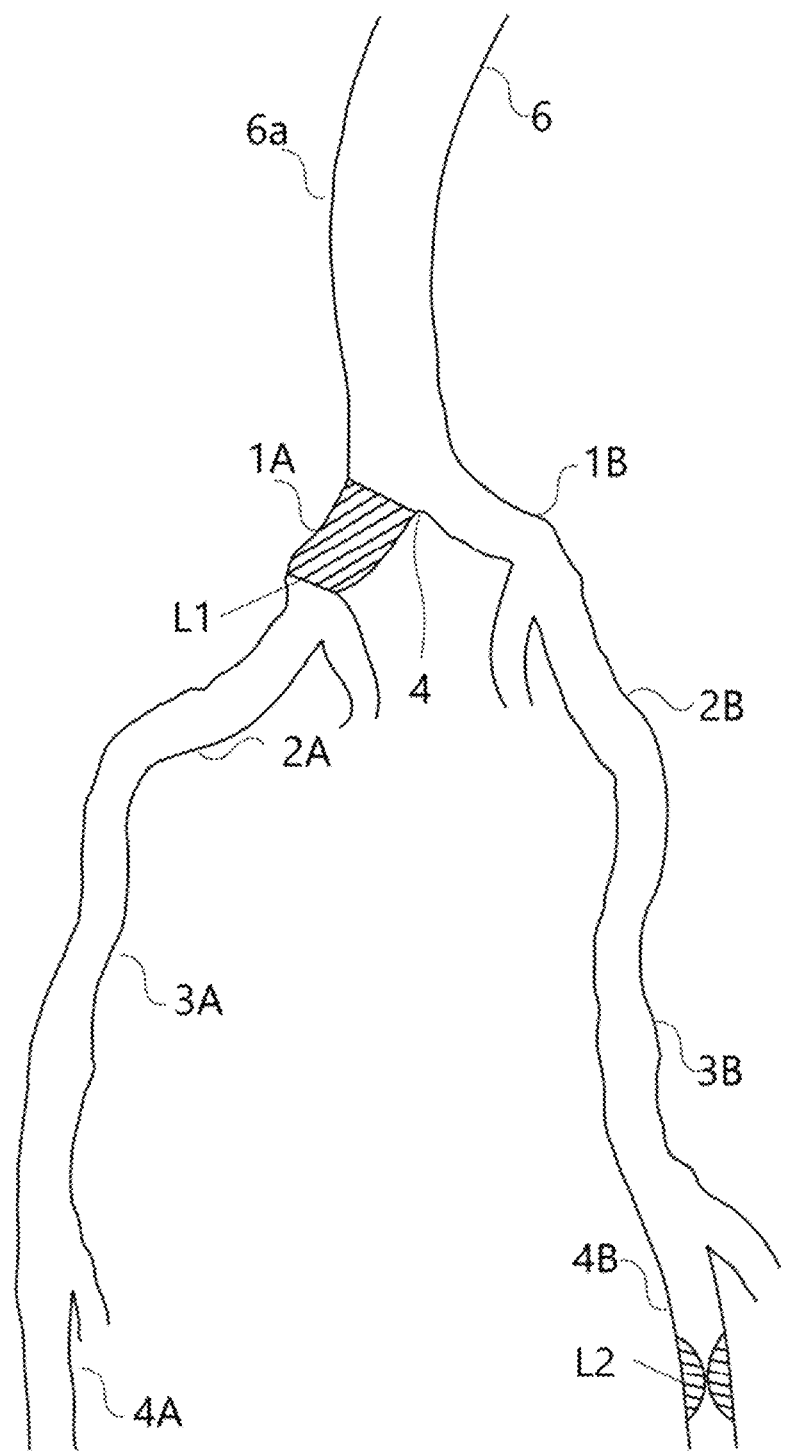
FIG. 14 is an explanatory drawing of a lesion in the treatment method according to the embodiment.

FIG. 14 is a schematic drawing illustrating positions of the lesions (L1, L2) in the lower limb arteries.

In this embodiment, prior to catheter treatment, image information relating to blood vessel conditions of a patient is obtained by image diagnosis such as angiography, CT (Computed Tomography) as diagnostic information on the patient, and the distance of the lesion from the aortailiac bifurcation 5, the positions, the number, the length, the degree of stenosis, the degree of curvature, and the hardness of the lesions are evaluated from the size, the shape, the calcification degree, and the existence of the blood flow of the blood vessel.

Alternatively, based on the guidelines of Trans Atlantic Inter-Society II, (TASC II) as a method of evaluating the symptoms of the patient's lower extremities, the severity of Fontaine classification due to symptoms, for example, Peripheral Arterial Disease (PAD), the severity of the Rutherford classification based on the function test such as the blood pressure of the patient may be used to determine, for example, the condition of the blood vessel of the patient. When evaluating the symptoms of a patient, the symptoms of the patient may be evaluated comprehensively in combination with the state of the lesion obtained from angiography or image inspection by CT as mentioned above. In the present embodiment, for example, it may be decided (or determined) to treat the lesion part farther from the branch part first based on the distance from the bifurcation part 5 of the right and left aorta iliac arteries to the lesion part.

In the present disclosure, the distance of the lesion from the aortailiac bifurcation 5 corresponds to the distance from the aortailiac bifurcation 5 to the lesion. The distance can be defined by the length of the blood vessel between the aortailiac bifurcation 5 and a proximal end of the lesion. The distance may be obtained, for example, on an image acquired by using a CT image or an intravascular image data, or alternatively, may be obtained by measurement using an image diagnosis catheter.

In this embodiment, it is verified that the occluded site L1 is present in the right common iliac artery 1A, the stenosed site L2 is present in the left superficial femoral artery 4B, and the occluded part L1 is more proximal to the aortailiac bifurcation 5 than from the stenosed site L2, and thus determination is made to perform treatment from the occluded site L1 first.

Figure 15:
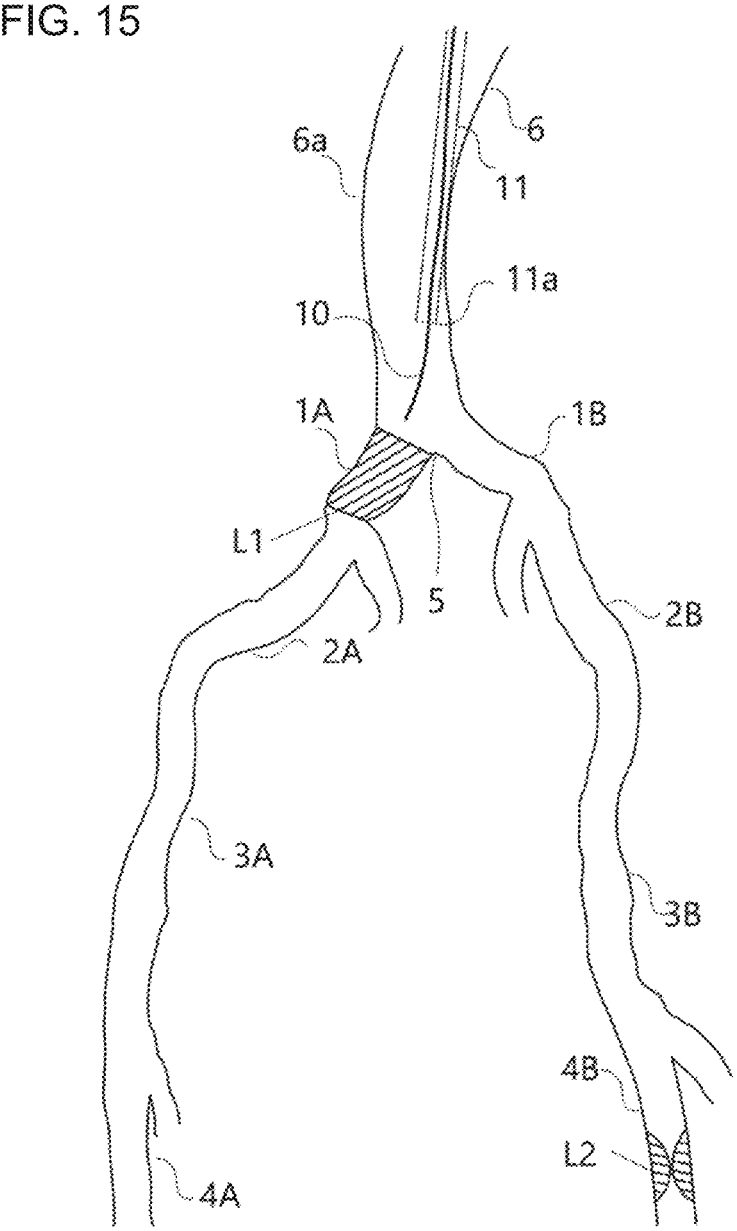
FIG. 15 is an explanatory drawing of the treatment method according to the embodiment illustrating a state just before selection of a blood vessel.

FIG. 15 illustrates a state in which the guiding catheter 11 is placed to a position in the vicinity of the aortailiac bifurcation 5. From this state, the catheter tip 11a and a distal end portion of the guide wire 10 placed in the guiding catheter 11 and introduced together with the guiding catheter 11 are directed to the occluded site L1 which is selected to be treated first.

Specifically, an opening portion of the catheter tip 11a is directed toward the right common iliac artery 1A with the guiding catheter 11 in contact with the left side of an abdominal aorta 6a, which is the opposite side of the right common iliac artery 1A with respect to the aortailiac bifurcation 5.

Figure 16:
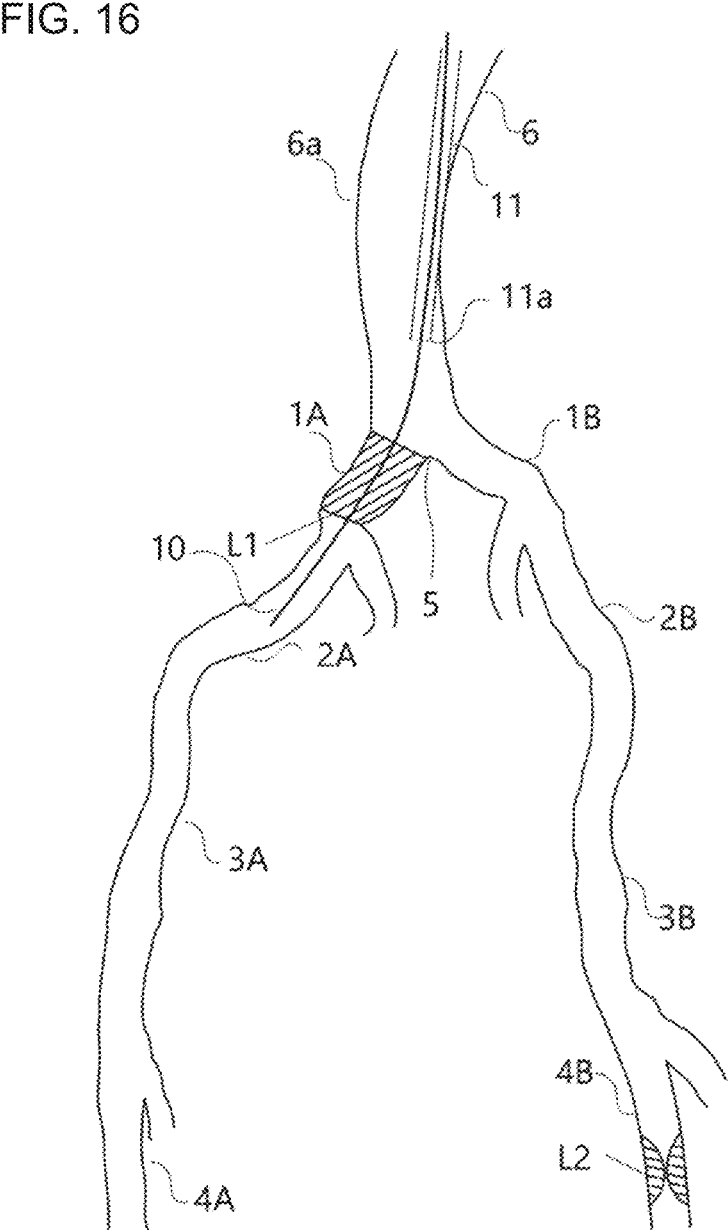
FIG. 16 is an explanatory drawing of the treatment method of the embodiment illustrating a state of placement of the catheter at a first lesion proximal to the bifurcation.

Subsequently, as illustrated in FIG. 16, the guide wire 10 is inserted into the right common iliac artery 1A side, and the guide wire 10 is placed in the right external iliac artery 2A. Subsequently, the catheter tip 11a is advanced to a position in the vicinity of the proximal side of the lesion, specifically, to a position between the abdominal aorta wall 6a and the right common iliac artery 1A along the guide wire 10, and places the guiding catheter 11 in the lower limb artery.

Figure 17:
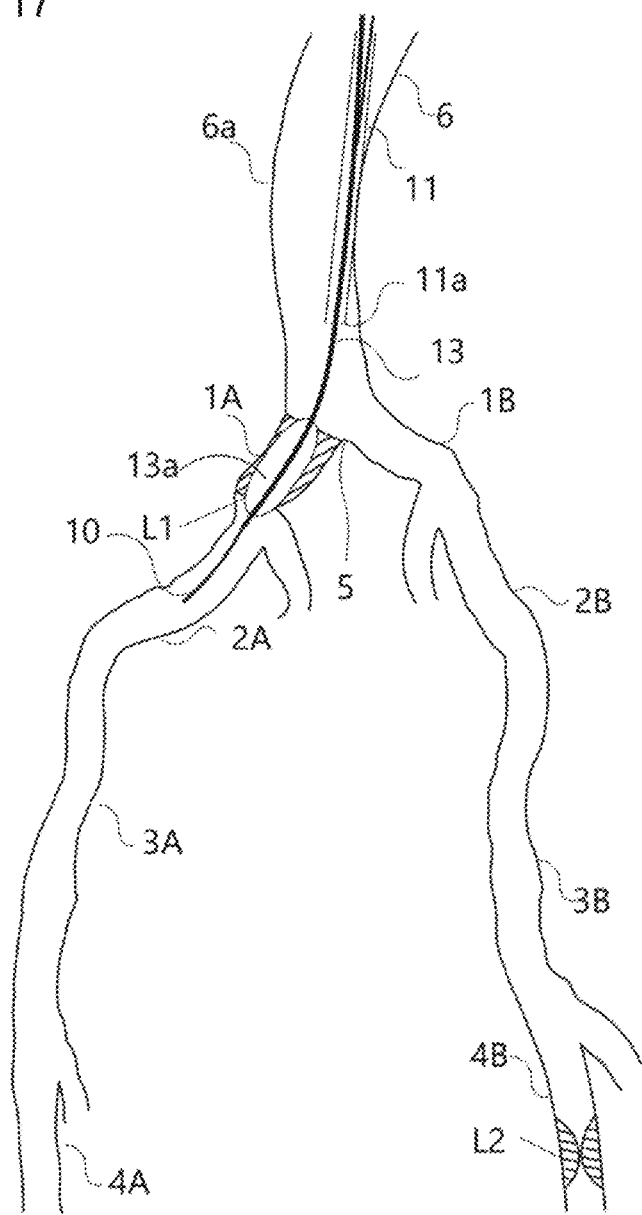
FIG. 17 is an explanatory drawing of the treatment method of the embodiment illustrating a state in which a balloon catheter is placed at the first lesion proximal to the bifurcation and the first lesion is treated.

FIG. 17 illustrates a state in which a therapeutic catheter is indwelled in the occluded site L1 and the occluded site L1 is treated. Specifically, in order to dilate the occluded site L1, which is a lesion of the right common iliac artery, the guide wire 10 is advanced through the occluded site L1 to, for example, the right external iliac artery 2A, then a balloon catheter 13 of a rapid exchange (RX) type, which is a therapeutic catheter, is advanced from the opening portion of the catheter tip 11a placed in the vicinity of the left side of the abdominal aorta 6a toward the occluded site L1 along the guide wire 10 and is delivered toward the occluded site L1, and a balloon 13a, which is a treatment portion, is placed in the occluded site L1.

Subsequently, an inflator (or inflation device) (not illustrated), for introducing a fluid into the balloon 13a of the balloon catheter 13, is attached to the balloon catheter 13 and a liquid is injected to dilate the balloon 13a, whereby the occluded site L1 is dilated.

The balloon catheter 13 operates the inflator after the treatment and deflates the balloon 13a, and is retracted and removed from the occluded site L1 to the hand-side. The guide wire 10 is also retracted to the hand-side in the same manner.

Note that when the balloon catheter 13 cannot enter the occluded site L1, an atherectomy catheter may be used as another therapeutic catheter prior to the balloon catheter 13 to make a hole in the occluded site L1, and then the balloon catheter 13 may be inserted.

Subsequently, treatment of the stenosed site L2 (lesion) distal to the aortailiac bifurcation 5 can be performed.

Figure 18:
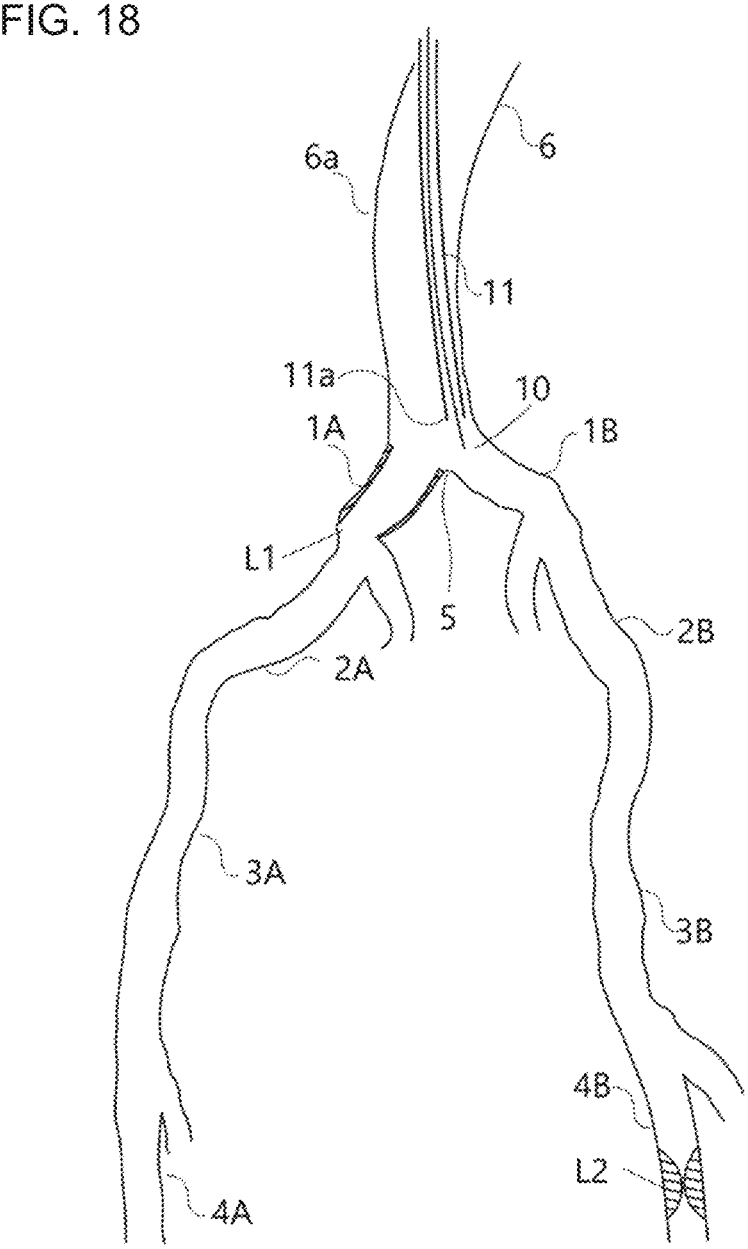
FIG. 18 is an explanatory drawing of the treatment method of the embodiment illustrating a state in which treatment of the first lesion in one of the blood vessels is completed and the catheter tip is directed toward the common iliac artery on the opposite side.

FIG. 18 is a drawing illustrating a state in which treatment of the occluded site L1 of the right common iliac artery 1A is completed first and then the catheter tip 11a is directed toward the left common iliac artery 1B for treating the stenosed site L2 of the left superficial femoral artery 4B, which is a lesion distal to the aortailiac bifurcation 5. The catheter of the guiding catheter 11 is free from deterioration such as significant change in shape, remaining bent, or separation of lubricious coating due to the treatment, and the direction of the catheter tip 11a can be changed relatively easily by an operation on hand-side.

In the case of a dual catheter, an inner catheter (not shown) is reinserted into the guiding catheter 11 along the guide wire 10 and proximal ends of the inner catheter and the guiding catheter 11 fit together.

Figure 19:
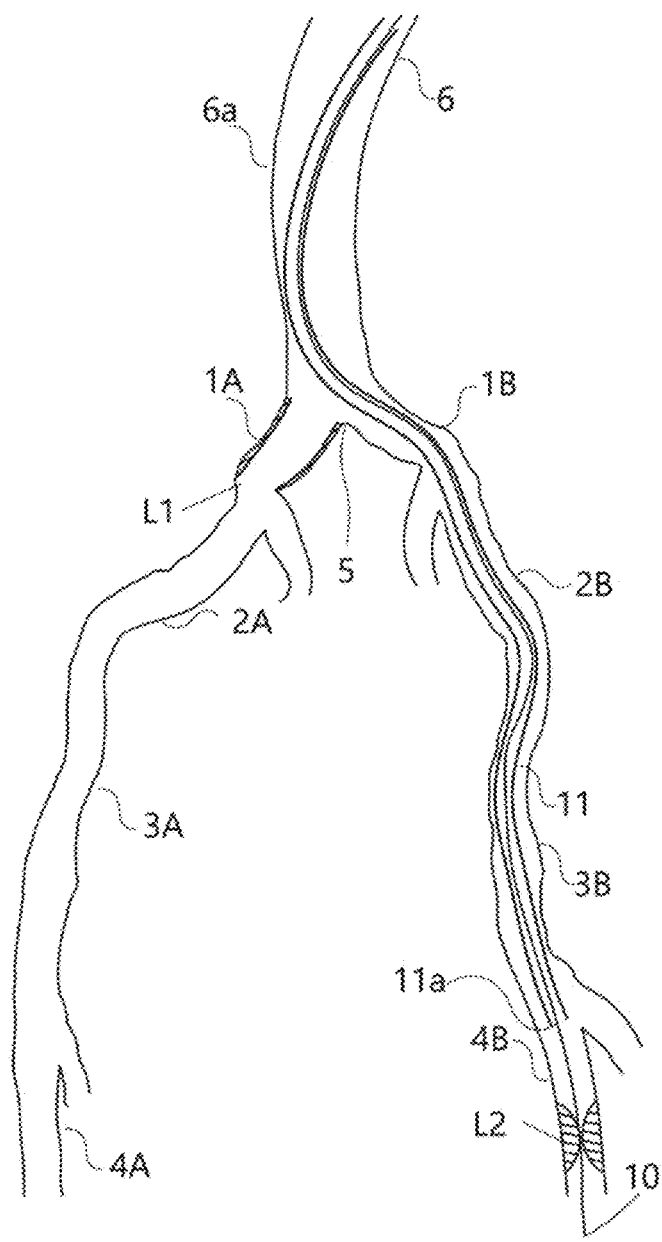
FIG. 19 is an explanatory drawing of the treatment method of the embodiment illustrating a state in which a guide wire reaches a second lesion distal to the bifurcation.

Subsequently, as illustrated in FIG. 19, the guide wire 10 is inserted into the left common iliac artery 1B, passed from the left external iliac artery 2B through the left common femoral artery 3B, and placed beyond the stenosed site L2 of the left superficial femoral artery 4B.

At this time, no significant bending remains in the guiding catheter 11 and thus the guide wire 10 to be passed through the guiding catheter 11 can be advanced rather easily although being in contact with the iliac artery. In accordance with an exemplary embodiment, the coating of the guide wire 10 does not separate from the guide wire 10 and relatively smooth placement can be achieved.

Subsequently, the catheter tip 11a is advanced along the guide wire 10 to a position in the vicinity of the proximal side of the lesion, specifically, for example, to a position beyond the bifurcation between the left superficial femoral artery 4B and the left deep femoral artery, and the guiding catheter 11 is placed in the lower limb artery.

Figure 20:
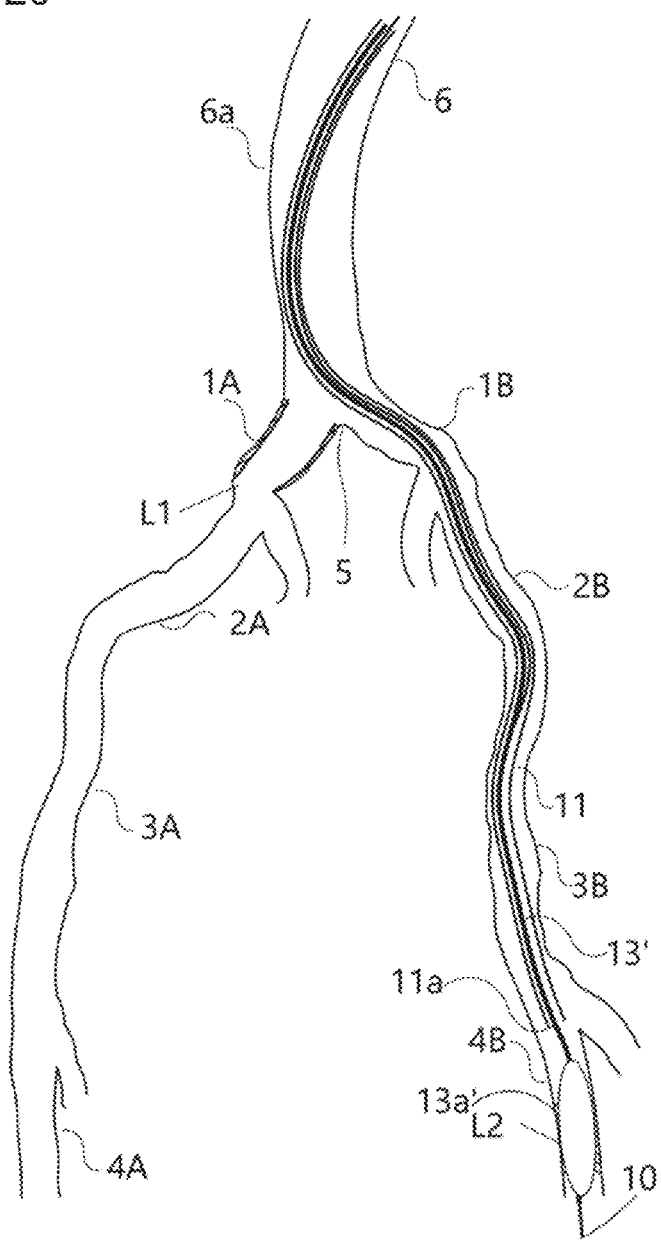
FIG. 20 is an explanatory drawing of the treatment method according to the embodiment illustrating a state in which the guiding catheter is placed before the second lesion and the second lesion is treated by the balloon catheter.

The inner catheter is removed, subsequently, as illustrated in FIG. 20, the balloon catheter 13' is advanced in the guiding catheter 11 in place, the balloon catheter tip is projected from the opening portion of the catheter tip 11a, and the balloon 13a' is placed in the stenosed site L2.

Subsequently, the inflator is attached to the balloon catheter 13', the balloon 13a' was dilated by injecting a liquid to dilate the stenosed site L2.

Figure 21:
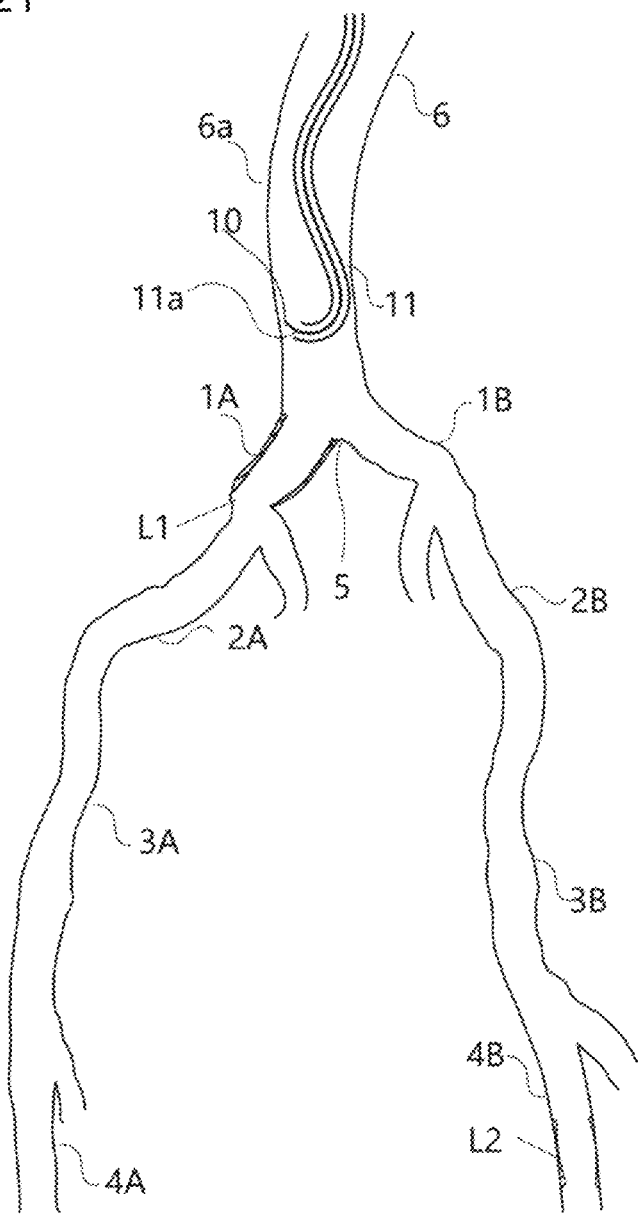
FIG. 21 is an explanatory drawing of the treatment method according to the embodiment illustrating a state in which the treatment of the second lesion is completed and the guide wire, the guiding catheter and the balloon catheter are retracted to a position proximal to the bifurcation on an operator side.

After treatment, as illustrated in FIG. 21, the balloon catheter 13' is removed, and the guiding catheter 11 and the guide wire 10 are retracted toward the hand-side and removed. At this time, the guiding catheter 11 has no separation of the coating, however, for example, there may remain deformation such as bending in the guiding catheter. In accordance with an exemplary embodiment, neither bending nor separation of coating was found on the guide wire 10.

In the embodiment described above, both of the lesions are treated by two balloon catheters having different dimensions in such a manner that the occluded site L1 is treated with the balloon catheter 13, and then the balloon catheter is replace with the new balloon catheter 13'. However, if usable, continuous treatment with one balloon catheter is also applicable (i.e., can be performed).

At this time, the guiding catheter 11 remains in the blood vessel, and thus replacement of the therapeutic catheter can be rather easily performed.

In particular, when the therapeutic catheter is a stent delivery catheter or a medicine coated balloon, the function is diminished by one treatment, and thus replacement may be essential.

Subsequently, when the treatment is not performed by using the guiding catheter 11, the guiding catheter 11 is removed out of the blood vessel together with other devices as-is to end the treatment.

Next, a case where the lesion distal to the aortailiac bifurcation 5 is treated first, specifically, a case where the stenosed site L2 of the left superficial femoral artery 4B is treated first will be described as a comparative embodiment.

Figure 22:
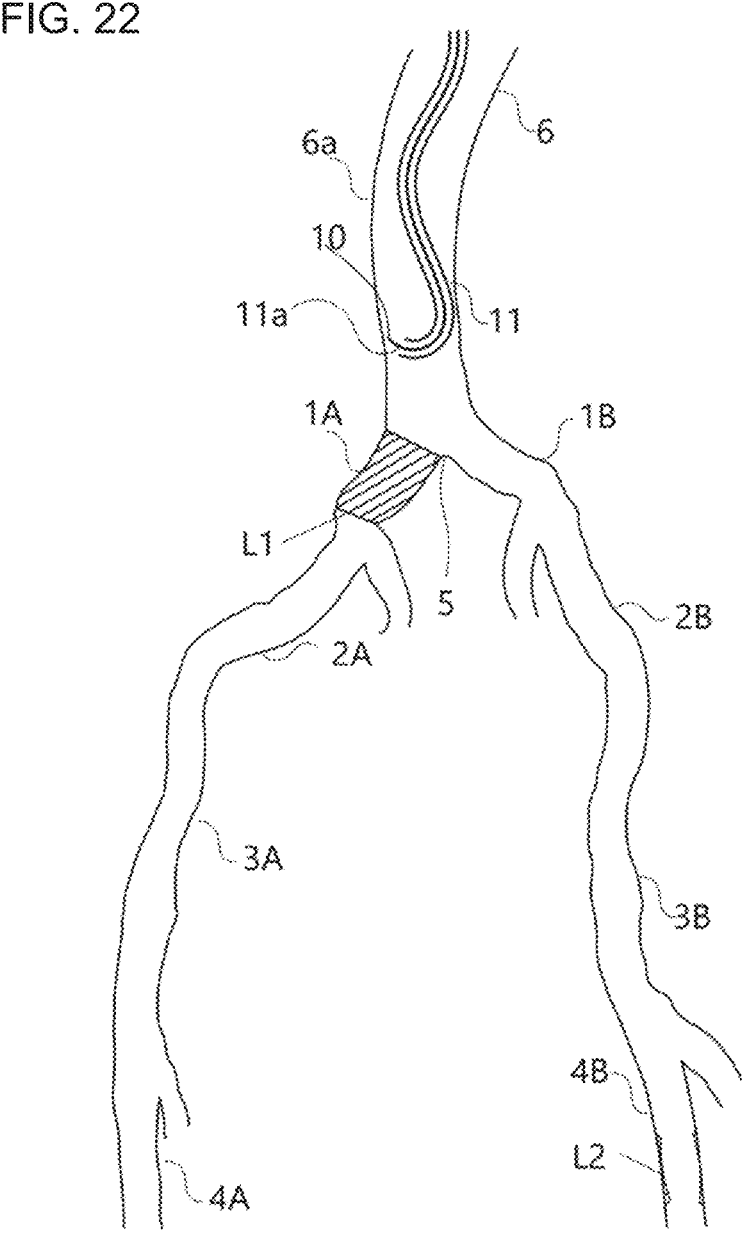
FIG. 22 is an explanatory drawing of the treatment method of a comparative embodiment illustrating a state in which the treatment of the second lesion distal to the bifurcation is completed and the guide wire, the guiding catheter, and the balloon catheter are retracted to a position in the vicinity of the proximal side of the bifurcation on the operator side.

FIG. 22 illustrates a state in which the stenosed site L2 which is a lesion distal to the aortailiac bifurcation 5 is dilated first. The guiding catheter 11 remains bent as a result of treatment, and the occluded site L1 remains in the right common iliac artery 1A.

When the balloon catheter 13, the guide wire 10, and the guiding catheter 11 are retracted to the aorta after the treatment, the guiding catheter 11 remains bent as illustrated in FIG. 22. This is substantially the same state as in FIG. 21 except that the occluded site L1 remains in the right common iliac artery 1A.

Figure 23:
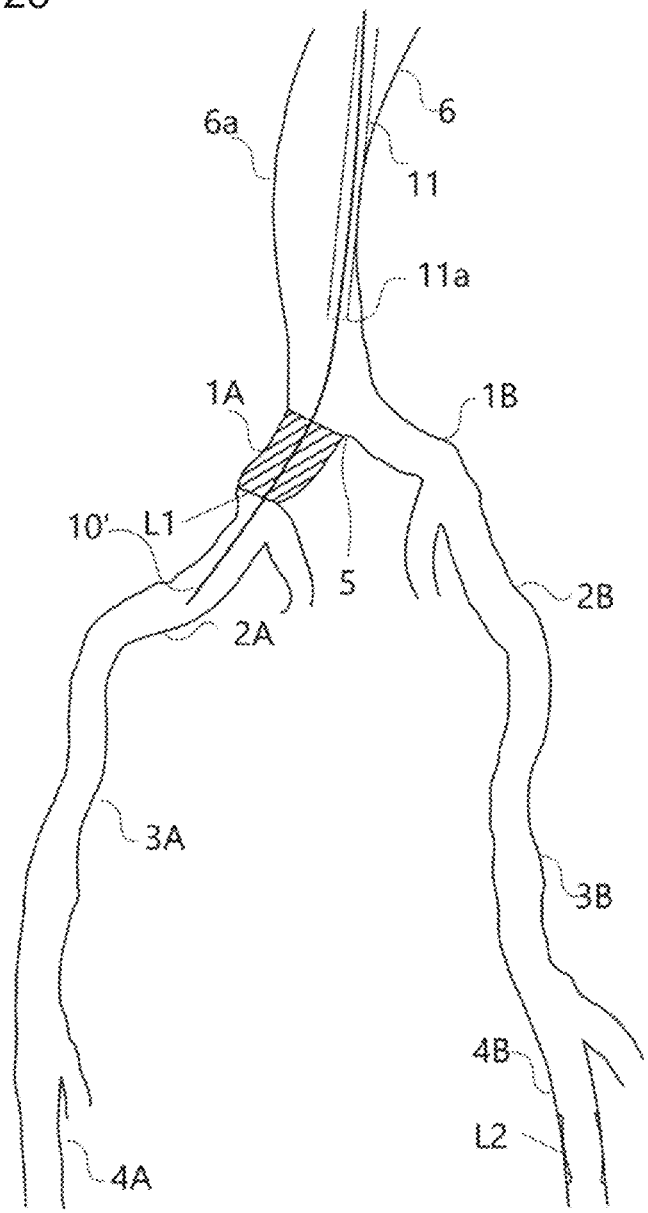
FIG. 23 is an explanatory drawing of the treatment method of the comparative embodiment in which the second lesion distal to the bifurcation is treated first, illustrating a state in which since the guiding catheter is significantly deformed, the guiding catheter can be straightened using a stiff guide wire having a relatively large tip load and the guiding catheter tip is directed to the first lesion.

Subsequently, the occluded site L1 of the right common iliac artery 1A is treated, and the guide wire 10 needs to be directed towards the right common iliac artery 1A. Since the guiding catheter 11 remains bent and the catheter tip 11a is directed in an unexpected direction, it may take time to direct the guide wire 10 to the entry port of the right common iliac artery 1A. Alternatively, as illustrated in FIG. 23, the guide wire can be replaced with a new hard-type guide wire 10' for treatment so as not to be affected by the remaining bent of the guiding catheter 11 for performing treatment.

Alternatively, as illustrated in FIG. 22, when the guiding catheter 11 is deformed in an unexpected shape, the guiding catheter 11 may not be placed at an expected position. In particular, in the case of the occlusion of the common iliac artery that does not allow insertion of the catheter tip 11a into the lower limb arteries, the guiding catheter 11 needs to be only supported by the blood vessel of the arm and the aorta wall.

Depending on the angle between the catheter tip 11a and the entry port of the common iliac artery, the guide wire 10 and the therapeutic catheter may move unintentionally such that the guide wire 10 may not be able to be pushed inward or, in contrast, the therapeutic catheter may be pushed too strongly (i.e., with excessive force) and can cause vascular dissection.

Figure 24:
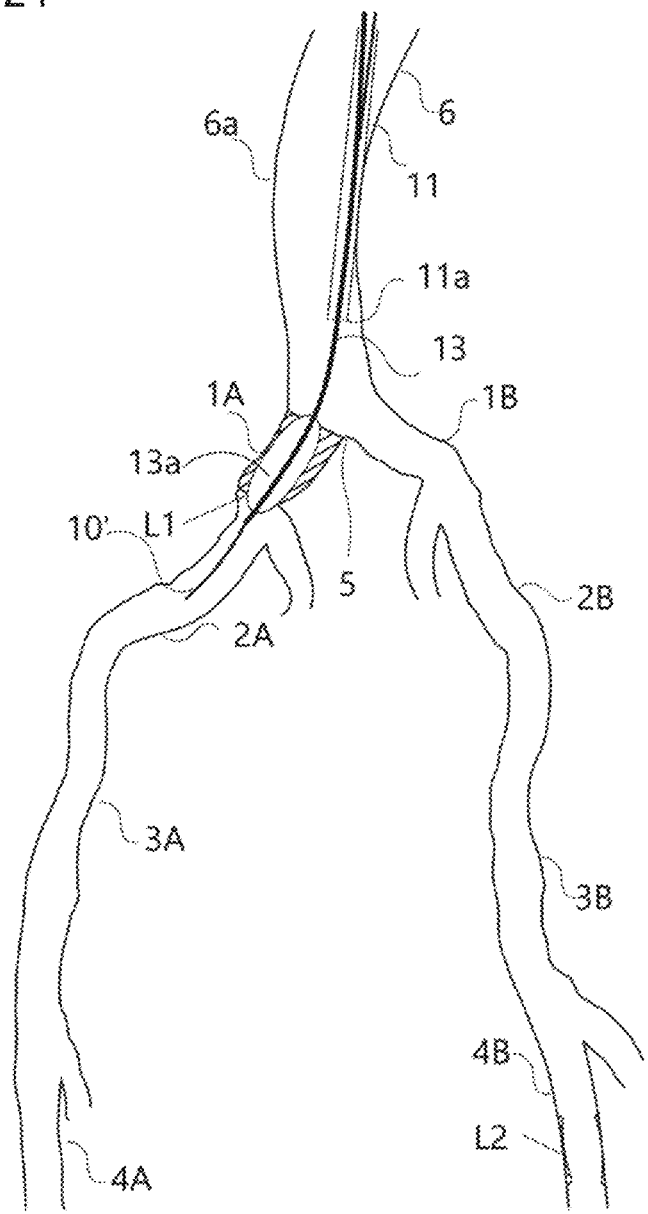
FIG. 24 is an explanatory drawing of the treatment method of the comparative embodiment illustrating a state in which, from the state described in FIG. 23, the guiding catheter is placed between the right common iliac artery and the abdominal aorta along the guide wire and the balloon catheter is placed in the lesion, and then the lesion is treated.

Subsequently, as illustrated in FIG. 24, the balloon catheter 13 is inserted along the guide wire 10' and the balloon 13a is placed in the occluded site L1, then a liquid is injected from the inflator into the balloon catheter 13 to dilate the balloon 13a, so that the occluded site L1 is dilated.

After the treatment, the inflator is operated to deflate the balloon 13a, the balloon catheter 13, the guiding catheter 11, and the guide wire 10 are retracted toward the hand-side, and then the balloon 13a, the balloon catheter 13, the guiding catheter 11, and the guide wire 10 are removed from the body to complete the treatment.

In the comparative example, the guide wire 10' of a stiff type is required in this manner and thus the treatment time was increased.

In this manner, the treatment of the lower limb arteries with the lesions in on the left and right is achieved efficiently with relatively less burden on the patient by the treatment method according to the steps described in the embodiment.

Subsequently, the present disclosure will be described in detail based on the preferred examples. However, it is needless to say that the disclosure is not limited to the contents of the examples.

EXAMPLE 1

An interventional device used in a treatment method included: an introducer sheath 12 including a dilator and a hemostasis valve and having an outer diameter of 2.8 mm, an inner diameter of 2.4 mm at the tip portion, and an entire length of 130 mm; a guiding catheter 11 having an outer diameter of 2.4 mm, an inner diameter of 2.2 mm, and an entire length of 1550 mm; a rapid-exchange type balloon catheter 13 having a balloon size of 8 mm in a dilated state, a balloon length of 40 mm, and an entire length of 2000 mm and a rapid-exchange type balloon catheter 13' having a balloon dimension of 6 mm in a dilated state, a balloon length of 100 mm, and an entire length of 2000 mm as a therapeutic catheter for performing treatment in the occluded site L1 and the stenosed site L2; and a guide wire 10 (an entire length of 3800 mm) having an outer diameter of 0.9 mm. A maximum length of projection of the balloon catheter 13 from a catheter tip 11a when inserted into the guiding catheter 11 was 400 mm.

In accordance with an exemplary embodiment, the guiding catheter 11 is a dual catheter combined with an inner catheter (an outer diameter of 2.1 mm, an inner diameter of 1.1 mm, and an entire length of 1600 mm, not illustrated). The maximum length of projection was 30 mm.

By using these interventional devices, a treatment simulation was performed for a blood vessel model as described below.

The interventional device was punctured into a left radial artery 30 of a patient having a occluded site L1 in the right common iliac artery 1A and a stenosed site L2 in the left superficial femoral artery 4B, and a stenosed site L2 in a right external iliac artery 2B, the guide wire 10 was placed in a blood vessel, and then the introducer sheath 12 was inserted, and then the guiding catheter 11 was introduced through the introducer sheath 12 after the dilator has removed.

Subsequently, the guiding catheter 11 was advanced from the left radial artery 30 to an abdominal aorta 6a of the patient so that the catheter tip 11a proceeded along the guide wire 10 to a position in the vicinity of the aortailiac bifurcation 5 on the aorta 6 side.

In order to treat the occluded site L1 of the right common iliac artery 1A, which was located proximal to the aortailiac bifurcation 5 first, the catheter tip 11a was placed so as to be directed toward an entry port of the right common iliac artery 1A. At this time, the guiding catheter 11 attached the left side of the abdominal aorta 6a.

The guide wire 10 was penetrated through the occluded site L1 by an operation of the guide wire 10 on hand so as to press the distal end portion of the guide wire 10 against the occluded site L1 in a state of supporting the guide wire 10 with the guiding catheter 11. The number of times of trial was once.

The inner catheter was removed, subsequently, the balloon catheter 13 of the rapid exchange (RX) type was projected to the occluded site L1 side along the guide wire 10 and delivered to the occluded site L1, and a balloon 13a was placed in the occluded site L1.

Subsequently, an inflator was attached to the balloon catheter 13, the balloon 13a was dilated by injecting a liquid to dilate the occluded site L1. After the treatment, the balloon catheter 13 was deflated, by operating the inflator of the balloon catheter 13, the balloon 13a was deflated and retracted from the occluded site X1 to the hand-side (i.e., proximal side) and removed. Subsequently, the guiding catheter 11 and the guide wire 10 were retracted to the hand-side in the same manner.

The inner catheter is reinserted, and, a hand-hub of the guiding catheter 11 was rotated to direct the catheter tip 11a toward the left common iliac artery 1B. The guide wire 10 is inserted into an entry port of the left common iliac artery 1B, passed from the left external iliac artery 2B through the left common femoral artery 3B, and placed beyond the stenosed site of the left superficial femoral artery 4B. The number of times of trial was once.

Subsequently, the catheter tip 11a was placed in the stenosed site L2 of the left superficial femoral artery 4B along the guide wire 10.

The balloon catheter 13' was advanced into the guiding catheter 11 in place to project the balloon catheter from the catheter tip 11a, and the balloon 13a' was placed in the stenosed site L2. The inflator is attached to the balloon catheter 13', and a liquid is injected to dilate the balloon 13a' as the treatment portion and the stenosed site L2 are expanded.

After treatment, the balloon catheter 13', the guiding catheter 11, and the guide wire 10 are retracted toward the hand-side (proximal side), and the balloon catheter 13', the guiding catheter 11, and the guide wire 10 are removed from the body. At this time, although the guiding catheter 11 was found to remain bent within a range of 300 mm from the catheter tip 11a toward the proximal side, removal was successfully done without problem.

The duration of the treatment simulation from puncture to removal was 30 minutes.

EXAMPLE 2

The same method as Example 1 was performed except that puncture site was a right radial artery 31.

The duration was 40 minutes. The guide wire 10 erroneously entered an ascending aorta instead of intended descending aorta from the brachiocephalic artery, and, after placement of the guiding catheter 11, the guiding catheter 11 was distorted when the balloon catheter 13 was inserted and pulled out, and thus meandering (prolapse) toward the ascending aorta was about to occur, which occurred due to an additional operation to clear distortion by pulling a hand-hub of the guiding catheter 11 to the hand-side.

COMPARATIVE EXAMPLE 1

Here, except that a stenosed site L2 of a superficial femoral artery 4B distal to an aortailiac bifurcation 5 was treated first, a catheter tip 11a was placed to the aortailiac bifurcation 5 in the same method as in Example 1.

In order to treat the stenosed site L2 of the left superficial femoral artery 4B first, the catheter tip 11 a was placed toward an entry port of a left common iliac artery 1B. At this time, a guiding catheter 11 attaches the right side of the abdominal aorta 6a.

The guide wire 10 was passed through the stenosed site L2 by an operation of the guide wire 10 on hand so as to press a distal end portion of the guide wire 10 against the stenosed site in a state of supporting the guide wire 10 with the guiding catheter 11. The number of times of trial was once. Subsequently, a balloon catheter 13' of a rapid exchange (RX) type was projected to the stenosed site L2 side along the guide wire 10 and delivered to the stenosed site L2, and the balloon 13a' was placed in the stenosed site L2.

Subsequently, an inflator was attached to a balloon catheter 13', the balloon 13a' was dilated by injecting a liquid to dilate the stenosed site L2. After the treatment, by operating the inflator of the balloon catheter 13', the balloon 13a' was deflated and retracted from the stenosed site L2 to the hand-side, and then the guiding catheter 11 and the guide wire 10 were retracted to the hand-side in the same manner.

Next, although the catheter tip 11a was directed toward the right common iliac artery 1A by rotating a hand-hub of the guiding catheter 11, the guide wire 10 was not directed toward the right common iliac artery 1A and thus cannot be inserted because the guiding catheter 11 was significantly deformed. Although the tip of the guiding catheter can be straightened by replacing the guide wire with a stiff-type guide wire 10' having a large tip load. However, since the operation was rather difficult, the balloon catheter 13' was removed.

Furthermore, an inner catheter was reinserted along the guide wire 10' and the guiding catheter 11 and the guide wire 10' could be directed toward the right common iliac artery 1A.

Subsequently, the occluded site 41 of the right common iliac artery was treated in the same manner as Example 1. Specifically, the guide wire 10 penetrated through the occluded site L1 by an operation of the guide wire 10 on hand so as to press the distal end portion of the guide wire 10 against the occluded site L1 in a state of supporting the guide wire 10 with the guiding catheter 11. The number of times of trial was once.

The inner catheter was subsequently removed, and a balloon catheter 13 of the rapid exchange (RX) type was projected (i.e., advanced) to the occluded site L1 side along the guide wire 10 and delivered to the occluded site L1, and the balloon 13a was placed in the occluded site L1.

Subsequently, an inflator was attached to the balloon catheter 13, the balloon 13a was dilated by injecting a liquid to dilate the occluded site L1. After the treatment, the balloon catheter 13 was deflated, by operating the inflator, and the balloon catheter 13 is retracted from the occluded site X1 to the hand-side (i.e., proximal side) and removed. Subsequently, the guiding catheter 11 and the guide wire 10 were retracted to the hand-side in the same manner.

The operation time was 60 minutes.

COMPARATIVE EXAMPLE 2

The same method as Example 1 was performed except that a puncture site was a right radial artery. The duration was 70 minutes. The guide wire 10 erroneously entered an ascending aorta from the brachiocephalic artery, and, after placement of the guide catheter 10, and thus meandering (prolapse) toward the ascending aorta was about to occur once when the balloon catheter 13 was inserted and pulled out, and the catheter was pulled back to the hand-side to clear the distortion.

The reason is that the balloon catheter 13 used for the treatment of the lesion L2 distal to the bifurcation first was removed, the inner catheter was reinserted, the guiding catheter was reassembled, the inner catheter was removed, and the balloon catheter 13 was reinserted in order to place the balloon 13a in the vicinity of the lesion L1 proximal to the bifurcation.

V. Diagnostic Method Based on Reinforcement-Learning Using the Result of Treatment In contrast to the hemostatic time and the duration (or time) of hospitalization can be reduced by less invasive treatment, an increased operation time increases not only a patient's burden, but also labor costs of a surgeon.

Therefore, effects due to the less invasive treatment may be offset by cost effectiveness.

In accordance with an exemplary embodiment, Markov Decision Process (MDF) was used to obtain a learning model of a diagnostic method based on reinforcement-learning using the result of treatment.

The term "Markov" comes from Markov property, and represents a property that only the current state (s) is responsible for next behavior as represented by t(s).

The learning model was obtained in a manner given below.

States (S) is a current situation (for example, patient information, position of lesions, and catheter to be used), and represents a specific aspect of treatment of lower limb arteries by TRI approach.

Model (T(s, a, s')(=P(s'|s, a))) is a learning model, T is a Transition (T), and when a behavior "a" is taken under state of s, the situation s' is brought about.

However, a probabilistic expression (P(s'|s, a)) is used because such a situation that even when "a" is selected, nothing may be invoked.

Usage of a catheter guide wire, and movement and therapeutic catheter are expressed by T(s, a, s').

Actions (A(s), A) is an action, and a function is A(s) if the action taken by a good situation changes a behavior.

In accordance with an exemplary embodiment, the action can correspond to the currently selected catheter, etc., or which catheter is to be used, or which one of a lesion distal to a bifurcation or a lesion proximal to the bifurcation is to be treated first.

Rewards (R(s), R(s, a), R(s, a, s')) is remuneration and status, and is remuneration obtained from the action in the corresponding situation. This remuneration is self-assessment (immediate remuneration), except for the last result.

Policy (π(a|s)) is strategy and is a function that returns which action "a" is to be taken in the situation s. A surgeon such as a physician (decision maker) selects and decides Policy.

Executable treatment actions and their probabilities is probabilistic because there are cases where placement is successfully achieved by the first trial, where puncture has occurred when a guide wire 10 was advanced, where a guiding catheter 11 cannot pass, where a balloon catheter 13 does not pass, and so forth.

Figure 12:
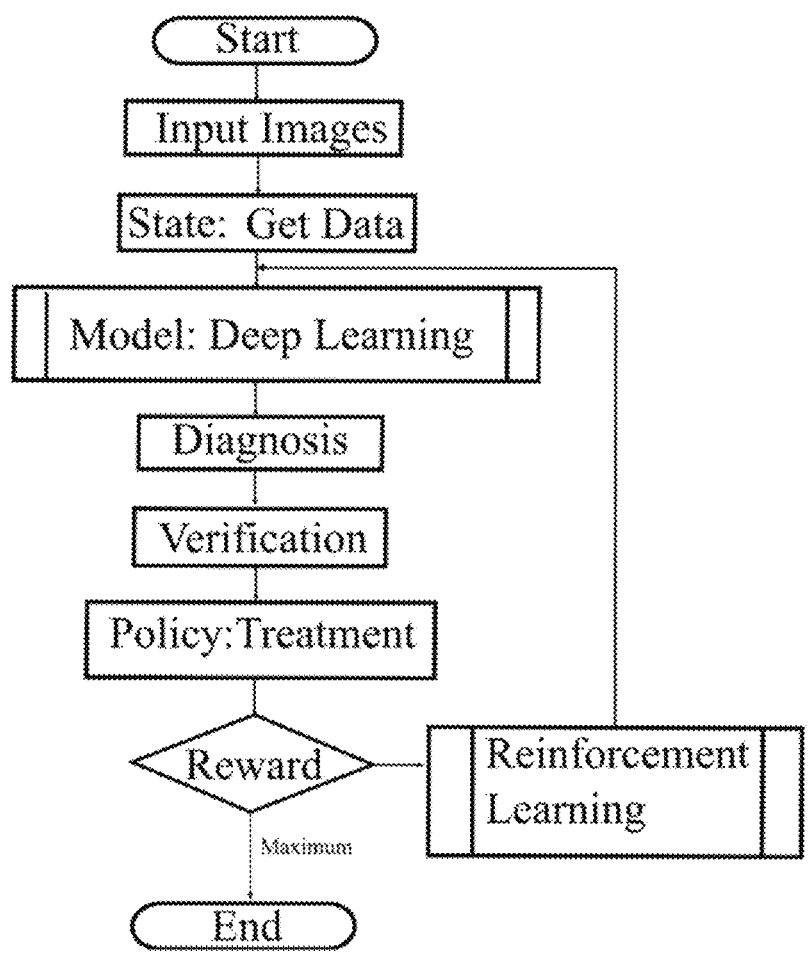
FIG. 12 is a conceptual illustration of the diagnostic method based on reinforcement-learning using a result of treatment according to the embodiment.

Thus, the treatment to be performed is represented by (T (s, a, s')(=P (s'|s, a)). As illustrated in FIG. 12, the treatment method is intended to treat lesions of lower limb arteries by a relatively less invasive treatment. However, it is also necessary to optimize the treatment by maximizing the remuneration in terms of time.

Therefore, a concept of discount in time is introduced, and the remuneration is reduced if the operation time is long even though the same effects of treatment are obtained. In other words, in order to optimize the strategy, concept of optimizing the sum of the remuneration and making discount of the remuneration according to the time is introduced. This is expressed by Equation (8).

$$U^{\pi}(s) = E\left[\sum_{t}^{\infty} \gamma^{t} R(s_{t}) \mid \pi, s_{0} = s\right] \tag{8}$$

Sum of remuneration=$U^\pi(s)$: The sum of the remuneration when a strategy $\pi$ is performed from the state s ($\pi$, $s_0=s\pi$), and is approximately equal to 1 at the discount=$\gamma$: $0 \le \gamma < 1$ according to the time.

Aiming at the strategy to maximize "the sum of remuneration taking the discount in terms of time into account", this optimal strategy is expressed by $\pi^*$.

In an optimal strategy, a person essentially acts to maximize the remuneration. Therefore, it is expressed by Equation (9).

$$U(s) = R(s) + \gamma \max_{s'} \sum T(s, a, s')U(s') \qquad (9)$$

The term "$\gamma$ max" means to choose the maximum. From s', which is the destination of the transition from s, one acts towards s', where the sum $U(s')$ of the expected remuneration is greatest.

The optimal strategy $\pi^*$ means that, in any s, one acts to maximize the sum of remuneration from the current situation, and thus $U^\pi(s)$ defined at the beginning is expressed by Equation (8).

This equation (Equation (9)), called Bellman equation, can be used to exclude the strategic $\pi$ term from the expression, and can "calculate its remuneration regardless of the strategy chosen". That is, a model for calculating the optimal action only from a treatment setting (environment) can be formed.

Next, a description will be given of how to make the model constructed as described above learn.

In other words, the calculation is repeated backward from the state where the "last remuneration" is obtained. This repeated calculation is referred to as Value Iteration method. Value Iteration method uses the Bellman equation derived earlier to calculate the optimal action "only from treatment settings".

The procedure is as follows.
1. Establish a fixed remuneration.
2. For each states, the remuneration represented by Equation (10) obtained by executable a is calculated.

$$\gamma \Sigma T(s,a,s\alpha)U(s') \qquad (10)$$

3. The sum of remuneration $U(s)$ is calculated with the highest reward of a in 1.
4. Return to 1 until convergence (until update intervals of $U(s)$ is reduced), and repeat the update.

Finally, the treatment action has been proven that it converges to an expected value.

In this manner, estimation of a remuneration map "only from the treatment settings" is achieved by Value Iteration, and thus this procedure is suitable for a case of introducing the optimal action for inspecting all the behavior in all the situations.

Alternatively, Policy Iteration may be used to determine a temporary strategy, search for a remuneration within that range, and update the result.

Policy Iteration refers to repeating calculations until convergence, so that the calculation is repeated until $\pi_{t+1} \approx \pi_t$ that is, until the selected behavior is almost unchanged.

Policy Iteration first determines the appropriate (random) strategy $\pi_0$, calculates the "remuneration obtained from strategy" $U^{\pi 0}(s)$, and improves the strategy ($\pi_1$). It is expressed by steps as given below and Equation (11).
1. Determine the appropriate strategy ($\pi_0$).
2. Calculate $U^{\pi t}(s)$ based on strategy.
3. Update strategy $\pi_1$ to be $\pi_{t+1}$.
4. Return to 1 until convergence is reached, and repeat the update.

$$(\pi_{t-1} = \mathrm{argmax}_a \Sigma T(s,a,s')U^{\pi 0}(s')) \qquad (11)$$

In accordance with an exemplary embodiment, Policy Iteration can be suitable when T(s, a, s') is known, that is, when a transition destination is known in advance under each situation. In accordance with an exemplary embodiment, Policy Iteration can be preferable over Value Iteration Policy Iteration is earlier in terms of time than the Value Iteration, and thus the load on the computer can be relatively smaller.

In contrast, if the number of situations and the number of possible actions are relatively large in number, it can be very difficult for a human to set up either the Policy Iteration or Value Iteration.

In accordance with an exemplary embodiment, since the setting of the advance environment (learning model) is not required, Q-learning, which is a learning method of "Model-Free" may be performed.

Q-learning has a value Q that indicates the validity of rule for rule to be executed, and the value Q is updated each time the surgeon acts. As used herein the term "rule" is intended to mean a pair of a state and an action that the surgeon can take under the state.

In accordance with an exemplary embodiment, it can be assumed that the state in which one each of lesion is present in each of left and right lower limb arteries bifurcated from the aorta via the aortailiac bifurcation is st, and there are four actions a, b, c, and d which can be taken in this state.

In this case, diagnosis is performed for four types of treatment, a: the lesion proximal to the bifurcation is treated first by introducing from the left TRI, and then the lesion distal to the bifurcation is treated; b: the lesion proximal to the bifurcation is treated first by introducing from the right TRI, and then the lesion distal to the bifurcation is treated; c: the lesion distal to the bifurcation is treated first by introducing from the left TRI, and then the lesion proximal to the bifurcation is treated; and d: the lesion distal to the bifurcation is treated first by introducing from the right TRI, and then the lesion proximal to the bifurcation is treated.

At this time, the reinforcement-learning determines the action to be performed based on the 4 Q values, Q(st, a), Q(st, b), Q(st, c), Q(st, d). The action theoretically converges the Q value even at random if an infinite number of attempts are made.

To reduce calculation time and reduce the load of the calculator, it is preferable to choose an action having a high Q value with high probability in order to speed up the convergence.

Even though T (s, a, s') is unknown, if you take action a in the states once, then s' becomes apparent. Leaning is proceeded (i.e., continued) by repeating this "trial".

The first trial is represented by the following equation:

$$Q(s,a) \approx R(s,a) + \gamma \max_{a'} E[Q(s',a')] \qquad (12)$$

T (s, a, s') disappears, and is replaced by expected value (E[Q (s', a')]). By repeating the trial, the expected value finally makes Equation (12) above establish as almost equal ($\approx$) and achieves equality.

When the equality is satisfied, it means the probability value (Q(s,a)) and the expected value in actual action shown by Equation (13):

$$R(s,a) + \gamma \max_a E[Q(s',a')] \qquad (13)$$

are equivalent. Accordingly, accurate prospect of the remuneration is achieved, which means the completion of learning. The process of this learning is expressed by Equation (14).

$$Q(s,a) = Q(s,a) + \alpha(R(s,a) + \gamma \max_{a'} E[Q(s',a')] - Q(s,a)) \quad (14)$$

where α is a learning rate, and learns from the difference between expected value actual remuneration) and prospect. This difference (=error) is referred to as TD error (TD=Temporal Difference), the method of learning based on TD error is referred to as TD learning, and Q-learning is a kind of TD learning.

The Equation (14) can be expressed as Equation (15), and the table of the prospect of remuneration is referred to as Q-Table, when "What type of remuneration is obtained by what kind of behavior in what kind of state" is listed.

$$Q(s,a) = (1-\alpha)Q(s,a) + \alpha(R(a,s) + \gamma \max_a E[Q(s',a')]) \quad (15)$$

This expression can improve Q (s, a), but there remains the problem whether deciding a or not. The value that makes Q (s,a) greatest may be selected. However, exploration and exploitation dilemma (search/exploitation dilemma), which means loss of the possibility to reach unknown s' with high remuneration.

Alternatively, as an ε-greedy method, a method of making trial with the probability of ε, and then "greedy, that is, taking an action based on the known remuneration, or Deep Q-learning (DQN), which is a highly accurate approximation using Boltzmann distribution or ANN may be used by using Equation (16).

$$P(a|s) = \frac{e^{Q(s,a)/k}}{\sum_j e^{Q(s,aj)/k}} \quad (16)$$

The learning of ANN is based on an error propagation method (Back propagation), and by calculating the error with the correct answer and propagating the result in the backward direction, the learning model is adjusted so that the learning model becomes proximal to the correct answer.

First, Q (s, a) whose weight is θ, $Q_\theta(s, a)$ is defined as ANN, and the definition of error using the TD error of the above equation is represented by Equation (17) as follows.

$$L_\theta = E[\tfrac{1}{2}(R(s,a) + \gamma \max Q_{\theta i-1}(s',a') - Q_\theta(s,a))^2] \quad (17)$$

Rising to the second power is because of error, and multiplying by ½ is for erasing 2 which emerges when differentiation is made. When $(f(x)=x^2)$, $f'(x)=2x$. As can be seen from the configuration of the expression, the underlined portion (expected value) corresponds to a supervisor label (target) which is referred to as a supervised learning.

Then, the equation is differentiated and gradient used for propagation of errors is represented by the following Equation (18):

$$\nabla_\theta L_{\theta=E}[(R(s,a) + \gamma \max Q_{\theta i-1}(s',a') - Q_{\theta i}(s,a)) \nabla_\theta Q_{\theta i}(s,a)] \quad (18)$$

The reason why the value Q on the expected value side is as expressed by Equation (19) is that the expected value is calculated by using previous θ.

$$Q_{\theta i-1}(s',a') \quad (19)$$

As described above, $Q_{\theta i-1}(s',a')$ has a role of the label data in supervised learning. Therefore, although the term on the expected value of the equation includes θ, the single underlined portion of Equation (20) is not an object of differential when calculating the gradient.

In addition, since ANN has an increased parameter, Deep Q-learning may be performed according to the following method for shortening (or reducing) the calculation time.

For example, for information groups continuing temporarily and having a correlation, the state/behavior/remuneration/transition destination once experienced by Experience Replay method may be stored in memory, and may be sampled from the memory during learning.

In terms of expression, sampling from the values stored in the memory (D) is performed as described below with reference to Equation (20), and the calculated expected value (double underlined part) is used for learning.

$$L(\theta) = E_{s,a,r,s' \sim D}\left[\left(\underline{r + \gamma \max_{a'} Q(s', a', \theta)} - Q(s, a, \theta)\right)^2\right] \quad (20)$$

Since $Q_{\theta i-1}(s', a')$ included in the expected value depends on the previous weight θi−1 despite playing the role of label data, the lesion to be treated first may be changed in label from L1 to L2 as shown in Equation (21) in association with update of θ.

$$L(\theta) = E_{s,a,r,s' \sim D}\left[\left(\underline{r + \gamma \max_{a'} Q(s', a', \theta)} - Q(s, a, \theta)\right)^2\right] \quad (21)$$

For this reason, a method of extracting several samples from the information first, such as Experience Replay described above, creating a mini-batch, and fixing to be used for calculation of the expected value during learning may also be employed.

In the equation, by fixing θ⁻ used to calculate the expected value as follows, the expected value (double underlined portion) is stabilized, and after the learning is finished, θ⁻ is updated to θ, and then the procedure goes to the calculation of the next batch.

Clipping of remuneration means to fix the remuneration, and it is determined to 1 if it is positive and −1 if it is negative. Therefore, although weighting of the remuneration is not possible, learning becomes relatively easy to advance.

In the manner as described above, Deep Q-learning includes a method of approximating Q-learning in ANN, and at least three techniques for efficiently advancing learning as described above.

In accordance with an exemplary embodiment, an approximation by ANN has an advantage that a numerical vector can be received as an input of state s.

As the remuneration, an X-ray angiographic images before treatment and the X-ray angiographic images after the treatment may be compared to see the difference.

Alternatively, the X-ray angiographic images may be generated when all the lesions are removed. Simply removing the lesion from the pre-treatment image is also applicable, and comparing with an X-ray angiographic images of a state in which a stent is inserted into a blood vessel and the shape of the blood vessel is changed by being dilated by the stent is also applicable.

In this case, the operation time and a device used to reach the shape of the ideal form may be taken into account, and it may be compared with the case of securing the blood flow to the narrowed or obstructed part and the predicted time until the restenosis is subsequently performed.

The result of treatment simulation described above may be used to perform a diagnosis using reinforcement-learning using a treatment result.

The result of treatment may be provided to the reinforcement-learning as remuneration, but the remuneration may not be limited to the operation time but may be reevaluated by success and failure of the procedure itself that has healed the stenosed site, or by a long term prognosis after the treatment. Alternatively, the operation time, the number of devices used, and the cost of the device may also be used. Alternatively, labor costs or the number of surgical operations per day may also be used. In accordance with an exemplary embodiment, the shorter operation time may be preferable, but the difference from the scheduled time may also be used. If the prediction of time is not sufficient, such as too early from the scheduled time, the time loss will be increased as seen in the case where the patient is not prepared for surgery, especially if there is only one operating room.

Alternatively, time taken by the guide wire to reach or pass the lesion may be used to evaluate for a portion which needs time most, for example, having several bend in the blood vessel between the bifurcation and the lesion.

In the case of a complex lesion or in the case where determination of whether a catheter treatment or a bypass treatment is near the boundary, the staffing of the health care worker can be reserved to prevent the absence of a physician who can perform the bypass surgery.

Alternatively, the number of times of trial, the movement of the device to the number of times of erroneous entry on the contrast image, or the time required for perforation and treatment, etc., may be used, or a combination of these information may be used, and also feature quantity that is provided in reinforcement-learning may also be used.

In accordance with an exemplary embodiment, the output may be a predicted image after treatment, or the difference between the predicted image and the actual post-treatment image may be used for evaluation. Alternatively, evaluation may be performed based on the predicted image after the treatment when the lesion proximal to the bifurcation is treated first and the predicted image after the treatment when the lesion proximal to the bifurcation is treated first, or the difference when the lesion proximal to the bifurcation is treated first and the predicted image after the treatment when the lesion proximal to the bifurcation is treated first, and if there is no difference between the predicted images after the treatment, evaluation may be performed based on the operation time.

Any diagnosis and treatment that can be recognized by reinforcement-learning as data and used for learning may be performed, and the subject may be human body or animals for studies. Alternatively, a simulation using a blood vessel model can also be used, but in that case, data of video taken by a video camera under visible light to record motion of a device or lesion model, movements or lines of movement of a surgeon or a nurse may also be used.

The surgeon may be a person, or may be robotically supported or manipulated. In accordance with an exemplary embodiment, preferably, the robot has reinforcement-learned artificial intelligence, and the robot can be provided with an apparatus including a drive unit such as a rotating portion, a straight portion, and sensing unit such as an optical sensor or a pressure sensor, and an information display unit such as GUI.

If the compensation setting or expression is difficult, such as a high number of parameters, reverse reinforcement learning may be performed. The reverse reinforcement-learning estimates remuneration from actions taken by experts (skilled surgeons).

For example, reverse reinforcement-learning using linear programming method such as Maximum Entropy IRL, Maximum Entropy Deep IRL may also be used.

EXAMPLE 3

A learning model was created by K-fold crossing variation method by using X-ray angiographic images of a blood vessel model and 100 X-ray angiographic images of lower limb arteries having lesions in both of the left and right lower limb arteries which are disclosed in Internet and Documents with K=10. The selection probability order was evaluated for a, b, c, and d by diagnosis based on Deep Q-learning method and by validation based on noise imparting method.

For this learning model, the diagnosis was made by providing images after the treatment simulation of Examples 1, 2, and Comparative Examples 1 and 2, and data of treatment time as remuneration by the Deep Q-learning method. For a treatment simulation images, a selection probability order of Q values, Q (st, a), Q (st, b), Q (st, c), Q (st, d) was obtained based on X-ray angiographic images obtained using a commercially available X-ray diagnostic apparatus.

Table 1 shows that, in the order of a>b>d>c, the diagnosis of treating the lesion proximal to the bifurcation first had a higher order (i.e., higher priority) than the treatment method in which diagnosing the lesion distal to the bifurcation was performed. When a noise was added in the axial direction of the lesion, determination of the area to be treated first was changed from the left lower limb artery to the right lower limb artery.

From these results, it was estimated that the diagnosis to determine the lesion to be treated first is made by the distance from the bifurcation, especially, for example, the information indicating that lesion is proximal to the bifurcation.

Further, when the images after the treatment simulation and the operation time were input and the same image information is made to learn again, the order was changed to a>b>c>d, which means that the diagnosis that the lesion proximal to the bifurcation is to be treated first is the same, but the probability of selecting the left TRI becomes higher, and thus the left TRI had a higher selection probability than the right TRI as it goes distal to the bifurcation.

Accordingly, by providing remuneration (i.e., a reward or compensation) for shortening the time, machine-learning can be used to diagnose the treatment in a relatively short time.

Note that the remuneration is not limited to time, for example, remuneration may be nonclinical remuneration such as labor or cost, or even hospitalization period. Alternatively, long-term patency rates, reoperation rates, and average life expectancy after treatment based on evidence obtained in large-scaled clinical trials may be used.

Note that the diagnostic method, the validation method, and the treatment method may be a program for carrying out a program, a storage medium for holding a program, or data or a data structure. Alternatively, it may be a diagnostic device, a diagnostic system, or a robot that supports a surgeon, and it may be a medical device incorporating a diagnostic method and a validation method program, and a treatment device incorporating a program of a treatment method may be incorporated into the diagnostic apparatus.

Alternatively, each of two ANN, Generator and Discriminator, may be incorporated into one computer, or they may be incorporated separately in two computers to enhance the independence. The Generator and the Discriminator can vary the weights and differentiate the ANN by varying the weighting and biases of early machine-learning to reduce the learning time and required training data.

Diagnosis, treatment, and validation are made that a lesion proximal to the aortailiac bifurcation is to be treated first for patients with lesions in the left and right lower limb arteries by a person or the reinforcement-learned artificial intelligence. The number of times of inserting and pulling out a treatment catheter is reduced, and a catheter is placed relatively easily in an intended blood vessel, so that the burden on the patient can be alleviated, the number of catheters to be used may be reduced, and treatment may be completed in a relatively short time.

The detailed description above describes to a method of diagnosing which of one or more lesions in each of a plurality of blood vessels bifurcated from a blood vessel having bifurcations is to be treated first for treating the blood vessel by an intervention procedure. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

TABLE 1

Selection Probability of Treatment

| | TRI Entry | 1st Treatment | 2nd Treatment | Deep-learning | Q-learning |
|---|---|---|---|---|---|
| a | Left | near | far | 1 | 1 |
| b | Right | near | far | 2 | 2 |
| c | Left | far | near | 4 | 3 |
| d | Right | far | near | 3 | 4 |

A learning model is created by reading 80 out of 100 lower limb artery images published on the Internet and the selection probability ranking when 20 subjects are diagnosed

What is claimed is:

1. A treatment method of a patient having a lesion in each of left and right lower limb arteries connected via an aortoiliac bifurcation to an aorta, the treatment method comprising:
   verifying with reinforcement-learned artificial intelligence which of the respective lesions is more proximal to the aortoiliac bifurcation based on diagnostic information on the patient;
   training a machine-learning algorithm associated with the reinforcement-learned artificial intelligence with a number of medical devices used for completed treatments, a cost of the number of medical devices used for the completed treatments, and operation times for the completed treatments;
   determining that the lesion more proximal to the aortoiliac bifurcation is to be treated first based on determining an operation time, a number of medical devices, and a cost of medical devices for the treating of the lesion more proximal to the aortoiliac bifurcation and treating of a lesion more distal to the aortoiliac bifurcation after the treating of the lesion more proximal to the aortoiliac bifurcation with the machine-learning algorithm associated with the reinforcement-learned artificial intelligence;
   introducing a catheter from an artery of an arm of the patient, advancing and placing a catheter tip of the catheter to at least the aortoiliac bifurcation of the patient; and
   inserting a therapeutic catheter into a lumen of the catheter, projecting a therapeutic catheter tip of the therapeutic catheter from the catheter tip, and treating the lesion more proximal to the aortoiliac bifurcation first, and then projecting the therapeutic catheter tip of the therapeutic catheter from the catheter tip, and treating the lesion more distal to the aortoiliac bifurcation.

2. The treatment method according to claim 1, comprising:
   treating the lesion more distal to the aortoiliac bifurcation with the catheter.

3. The treatment method according to claim 1, comprising:
   treating the lesion more distal to the aortoiliac bifurcation with the therapeutic catheter.

4. The treatment method according to claim 1, comprising:
   removing the therapeutic catheter from the catheter after treating the lesion more proximal to the aortoiliac bifurcation; and
   treating the lesion more distal to the aortoiliac bifurcation with a second therapeutic catheter.

5. The treatment method according to claim 1, wherein the catheter is a guiding catheter, the method comprising:
   placing the catheter tip of the catheter to at least the aortoiliac bifurcation of the patient with a catheter assembly including an inner catheter inserted in a lumen of the guiding catheter.

6. The treatment method according to claim 1, further comprising:
   acquiring image information of the patient; and
   wherein the diagnostic information is the image information of the patient.

7. The treatment method according to claim 1, comprising:
   acquiring image information of the patient; and
   measuring a distance from the aortoiliac bifurcation to the lesion more proximal to the aortoiliac bifurcation from the image information.

8. The treatment method according to claim 1, wherein verifying with reinforcement-learned artificial intelligence of which of the respective lesions is more proximal to the aortoiliac bifurcation based on the diagnostic information on the patient comprises:
   detecting electromagnetic waves obtained through the patient by irradiating the patient with electromagnetic waves, and obtaining electromagnetic wave information on the patient based on a changed irradiated electromagnetic wave;
   identifying one or more lesions from the electromagnetic wave information; and
   acquiring distance information from the bifurcation to the respective lesions from the electromagnetic wave information.

9. The treatment method according to claim 8, comprising:
   selecting the electromagnetic waves from one or more of X-rays, magnetic field lines, ultrasound waves, infrared rays, and visible light.

10. The treatment method according to claim 8, further comprising:
    calculating distance information from the aortoiliac bifurcation for each of the respective lesions; and comparing the distance information from the aortoiliac bifurcation for each of the respective lesions to determine the lesion more proximal to the aortoiliac bifurcation.

11. A treatment method for treating a patient having a lesion in each of left and right lower limb arteries connected via an aortailiac bifurcation to the aorta, the treatment method comprising:
verifying with reinforcement-learned artificial intelligence which of the respective lesions is more proximal to the aortoiliac bifurcation based on diagnostic information on a patient;
training a machine-learning algorithm associated with the reinforcement-learned artificial intelligence with a number of medical devices used for completed treatments, a cost of the number of medical devices used for the completed treatments, and operation times for the completed treatments;
determining that the lesion more proximal to the aortoiliac bifurcation is to be treated first based on determining an operation time, a number of medical devices, and a cost of medical devices for the treating of a lesion more proximal to the aortoiliac bifurcation and the treating of the lesion more distal to the aortoiliac bifurcation after the treating of the lesion more proximal to the aortoiliac bifurcation with the machine-learning algorithm associated with the reinforcement-learned artificial intelligence;
introducing a catheter from an artery of an arm of the patient, advancing and placing a catheter tip of the catheter to at least the aortailiac bifurcation of the patient;
inserting a therapeutic catheter into a lumen of the catheter positioned, projecting a therapeutic catheter tip of the therapeutic catheter from the catheter tip, and treating the lesion more proximal to the aortoiliac bifurcation first;
projecting the therapeutic catheter tip of the therapeutic catheter from the catheter tip to treat the lesion more distal to the aortoiliac bifurcation second; and
reducing operation times spent performing the treatment of the lesions in the left and right lower limb arteries of the patient by the treating of the lesion more proximal to the aortoiliac bifurcation first and then the treating of the lesion more distal to the aortoiliac bifurcation.

12. The treatment method according to claim 11, comprising:
treating the lesion more distal to the aortoiliac bifurcation with the catheter.

13. The treatment method according to claim 11, comprising:
treating the lesion more distal to the aortoiliac bifurcation with the therapeutic catheter.

14. The treatment method according to claim 11, wherein after treating the lesion more proximal to the aortoiliac bifurcation, the treatment method further comprising:
removing the therapeutic catheter from the catheter; and
treating the lesion more distal to the aortoiliac bifurcation with a second therapeutic catheter.

15. The treatment method according to claim 11, wherein the catheter is a guiding catheter, the treatment method comprising:
placing the catheter tip of the catheter to at least the aortailiac bifurcation of the patient with a catheter assembly including an inner catheter inserted in a lumen of the guiding catheter.

16. The treatment method according to claim 11, further comprising:
acquiring image information of the patient; and
wherein the diagnostic information is the image information of the patient.

17. The treatment method according to claim 11, comprising:
acquiring image information of the patient; and
determining the lesion more proximal to the aortoiliac bifurcation and the lesion more distal to the aortoiliac bifurcation from the acquired image information of the patient.

18. The treatment method according to claim 11, further comprising:
detecting electromagnetic waves obtained through the patient by irradiating the patient with the electromagnetic waves, and obtaining electromagnetic wave information on the patient based on a change in the detected electromagnetic waves;
identifying respective lesions in each of the left and the right lower limb arteries from the electromagnetic wave information; and
determining the lesion more proximal to the aortoiliac bifurcation and the lesion more distal to the aortoiliac bifurcation.

* * * * *